(12) United States Patent
Kitagawa et al.

(10) Patent No.: US 7,696,380 B2
(45) Date of Patent: Apr. 13, 2010

(54) AMIDE-BASED COMPOUND, POLYOLEFIN RESIN COMPOSITION AND MOLDED PRODUCT

(75) Inventors: Hiroshi Kitagawa, Otsu (JP); Masahide Ishikawa, Uji (JP); Chiaki Ueoka, Nara (JP); Sukehiro Niga, Otsu (JP); Yohei Uchiyama, Joyo (JP)

(73) Assignee: New Japan Chemical Co., Ltd., Kyoto-shi (JP)

( * ) Notice: Subject to any disclaimer, the term of this patent is extended or adjusted under 35 U.S.C. 154(b) by 869 days.

(21) Appl. No.: 10/574,832

(22) PCT Filed: Oct. 8, 2004

(86) PCT No.: PCT/JP2004/015297

§ 371 (c)(1),
(2), (4) Date: Apr. 6, 2006

(87) PCT Pub. No.: WO2005/037770

PCT Pub. Date: Apr. 28, 2005

(65) Prior Publication Data

US 2007/0066687 A1 Mar. 22, 2007

(30) Foreign Application Priority Data

Oct. 17, 2003 (JP) ............................. 2003-358004

(51) Int. Cl.
*C07C 233/05* (2006.01)
(52) U.S. Cl. ........................ 564/153; 564/152; 252/401; 524/210; 524/227
(58) Field of Classification Search ................ 564/152, 564/153; 252/401; 524/210, 227
See application file for complete search history.

(56) References Cited

U.S. PATENT DOCUMENTS 5,973,076 A * 10/1999 Yoshimura et al. .......... 525/184
7,235,191 B2 * 6/2007 Schmidt et al. ............. 252/401

FOREIGN PATENT DOCUMENTS

| EP | 0776933 | 6/1997 |
|---|---|---|
| EP | 1715000 | 10/2006 |
| JP | 06-192496 | 7/1994 |
| JP | 06-234890 | 8/1994 |
| JP | 06-263969 | 9/1994 |
| JP | 7-242610 | 9/1995 |
| JP | 07-278374 | 10/1995 |
| JP | 07-309821 | 11/1995 |
| JP | 8-48838 | 2/1996 |
| JP | 2002-538255 | 11/2002 |
| JP | 3401868 | 2/2003 |
| WO | WO00/52089 | 9/2000 |
| WO | WO 02/46300 A2 | 6/2002 |
| WO | WO 03/102069 A1 | 12/2003 |

OTHER PUBLICATIONS

European Search Report dated Jul. 18, 2007.

* cited by examiner

*Primary Examiner*—Shailendra Kumar
(74) *Attorney, Agent, or Firm*—Kratz, Quintos & Hanson, LLP

(57) ABSTRACT

Disclosed are a mixture of at least two amide-based compounds represented by General Formula (1):

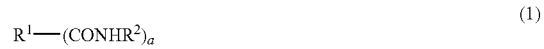

$$R^1\text{—}(CONHR^2)_a \tag{1}$$

wherein a represents an integer of 2 to 6, $R^1$ represents a $C_{2-30}$ saturated or unsaturated aliphatic polycarboxylic acid residue, and the aliphatic polycarboxylic acid has a valency of 2 to 6, and two to six $R^2$ groups are the same or different, and each represent a trans-2-alkylcyclohexylamine residue or a cis-2-alkylcyclohexylamine residue, the mixture having a content of a trans-2-alkylcyclohexylamine residue of at least 70 mole % but less than 100 mole % of the total 2-alkylcyclohexylamine residues in the mixture, or an all-trans amide-based compound wherein all of the 2 to 6 $R^2$ groups represent a trans-2-alkylcyclohexylamine residue; a polyolefin resin nucleating agent comprising the mixture or the all-trans amide-based compound; a polyolefin resin composition containing the amide-based compound or the mixture; a molded article obtainable by molding the composition.

9 Claims, 4 Drawing Sheets

AMIDE-BASED COMPOUND, POLYOLEFIN RESIN COMPOSITION AND MOLDED PRODUCT

This application is a 371 of PCT/JP04/15297, filed on Oct. 08, 2004.

TECHNICAL FIELD

The present invention relates to an amide-based compound, a process for producing the same, a polyolefin resin nucleating agent containing the amide-based compound, a polyolefin resin composition containing the nucleating agent, and a molded product thereof.

BACKGROUND ART

Polyolefin resins are used in various fields as materials for film forming, sheet forming, blow molding, injection molding, etc., due to their excellent moldability, mechanical characteristics, electrical properties, etc.

Although generally excellent in physical properties, the resins are low in transparency, crystallizability and rigidity. In some applications, outstanding properties inherently possessed by the resins are insufficiently exhibited and thus the application of such resins is limited under the present circumstances.

There have heretofore been proposals to use amide-based compounds so as to improve the transparency, crystallizability and rigidity of polyolefin resins (Japanese Patent No. 3401868, Japanese Unexamined Patent Publication No. 1995-242610, and WO 00/52089). Although such amide-based compounds are favorable in imparting transparency and mechanical strength (especially, rigidity) to polyolefin resins, development of a nucleating agent is sought which can impart further excellent physical properties to polyolefin resins.

In particular, the amide-based nucleating agent disclosed in Japanese Unexamined Patent Publication No. 1995-242610 imparts excellent transparency, crystallizability and rigidity to polyolefin resins, but the thermal stability and alkali resistance of the amide-based nucleating agents themselves are not satisfactory, and improvement in thermal stability and alkali resistance is demanded.

DISCLOSURE OF THE INVENTION

An object of the present invention is to solve the above-described problems, and thus provide an amide-based compound which has improved thermal stability and alkali resistance and which can produce a molded product with further improved transparency, crystallizability (heat-resistance) and rigidity; a process for producing the compound; a polyolefin resin nucleating agent containing the amide-based compound as an essential ingredient; a polyolefin resin composition comprising the nucleating agent, and a molded product thereof.

In view of the above circumstances, the inventors have conducted intensive research to solve the problems, and obtained the following findings.

(1) For the amide-based nucleating agent of Japanese Unexamined Patent Publication No. 1995-242610, commercially available 2-methylcyclohexylamine was used as a starting material. The 2-methylcyclohexylamine commercially available as a reagent or a industrial material is a mixture of its cis isomer and trans isomer wherein the ratio of trans isomer: cis isomer is about 68:32 (%, as determined by GLC (gas-liquid chromatography)), and mixtures with other compositions have not been sold. The amide-based nucleating agent prepared using this starting material and disclosed in Japanese Unexamined Patent Publication No. 1995-242610, such as 1,2,3,4-butanetetracarboxylic acid tetrakis(2-methylcyclohexylamide), 1,2,3-propanetricarboxylic acid tris(2-methylcyclohexylamide) or the like, also has amide moieties in the form of a mixture of trans configuration and cis configuration, so that the nucleating agent is actually a mixture of at least two amide-based compounds having different trans-configured amide moiety to cis-configured amide moiety ratios.

(2) The inventors found that the ratio of the trans-configured moiety to cis-configured moiety in the amide-based compound mixture is substantially the same as the ratio of the trans isomer:cis isomer (as determined by GLC) of the 2-methylcyclohexylamine used as the starting material, based on the results of a series of studies, such as comparison of the trans:cis ratio of the starting 2-alkylcyclohexylamine with the trans:cis ratio of the unreacted 2-alkylcyclohexylamine recovered after subjecting said starting 2-alkylcyclohexylamine to amidation reaction. Thus, the ratio of trans configured moiety:cis configured moiety in the amide-based compound mixture is controllable by the trans:cis isomer ratio of the starting material amine.

(3) The inventors also found that the proportion of the trans configured moiety in the amide-based compound mixture is linearly proportional to the ratio (namely, Ctrans to be described later) as defined by using 1) the absorbance (Atrans), as measured by FT-IR spectroscopy (Fourier Transform Infrared Spectroscopy), at a wavenumber at which the N—H stretching vibration absorption signal of the trans-2-alkylcyclohexylamine residue of the corresponding all-trans amide-based compound appears, and 2) the absorbance (Acis), as measured by FT-IR spectroscopy, at a wavenumber at which the N—H stretching vibration absorption signal of the cis-2-alkylcyclohexylamine residue of the corresponding all-cis amide-based compound appears.

Therefore, the ratio of the trans-configured moiety to cis-configured moiety in the amide-based compound mixture is verified by measuring the FT-IR spectrum of the amide-based compound mixture.

(4) The inventors conducted a research by varying the above-mentioned ratio of trans-configured moiety to cis-configured moiety in amide-based compounds, and found that the use of a nucleating agent comprising an amide-based compound mixture with a large proportion (content) of trans-configured moiety or an all-trans compound elevates the crystallization temperature of a polyolefin resin composition containing said nucleating agent, and improves the rigidity of a polyolefin resin molded product obtained from the polyolefin resin composition.

(5) A nucleating agent with a large proportion (content) of trans moiety in the amide-based compound mixture has a melting point higher than the nucleating agent disclosed in Japanese Unexamined Patent Publication No. 1995-242610, and is superior to it in thermal stability and alkali resistance.

Based on these findings, the inventors conducted further research and accomplished the present invention. The invention provides a mixture of at least two amide-based compounds represented by General Formula (1) or an all-trans amide-based compound represented by General Formula (1), a process for producing said mixture or said all-trans compound, a polyolefin resin nucleating agent comprising said mixture or said all-trans compound, a polyolefin resin composition containing said mixture or said all-trans compound (or said nucleating agent), a molded product thereof, and the like.

Item 1: A mixture of at least two amide-based compounds represented by General Formula (1):

wherein
  a represents an integer of 2 to 6,
  $R^1$ represents a $C_{2-30}$ saturated or unsaturated aliphatic polycarboxylic acid residue, and said aliphatic polycarboxylic acid residue has a valency of 2 to 6 (the same value as a), and
  the two to six $R^2$ groups are the same or different, and each represent a trans-2-alkylcyclohexylamine residue represented by General Formula (a):

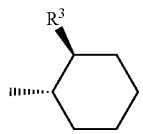

wherein $R^3$ represents a $C_{1-10}$ linear or branched alkyl group, or a cis-2-alkylcyclohexylamine residue represented by General Formula (b):

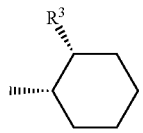

wherein $R^3$ represents a $C_{1-10}$ linear or branched alkyl group, the trans-2-alkylcyclohexylamine residue represented by General Formula (a) being present in a proportion of at least 70 mole % but less than 100 mole % of the total 2-alkylcyclohexylamine residues in the mixture.

Item 2: A mixture according to Item 1, wherein the trans-2-alkylcyclohexylamine residue represented by General Formula (a) is present in a proportion of at least 71.9 mole % but less than 100 mole % of the total 2-alkylcyclohexylamine residues in the mixture.

Item 3: A mixture according to Item 1 or 2, wherein $R^3$ is a $C_{1-6}$ linear or branched alkyl group.

Item 4. A mixture according to Item 1 or 2, wherein $R^3$ is methyl.

Item 5. A mixture according to any one of Items 1 to 4, wherein $R^1$ is a 1,2,3-propanetricarboxylic acid residue or a 1,2,3,4-butanetetracarboxylic acid residue.

Item 6. A mixture according to any one of Items 1 to 4, wherein $R^1$ is a 1,2,3-propanetricarboxylic acid residue, and the mixture has a trans 2-alkylcyclohexylamine residue absorbance proportion (Ctrans) of at least 56.3% but less than 72.0% as defined by equation (E):

$$Ctrans(\%) = [Atrans/(Atrans + Acis)] \times 100 \quad (E)$$

wherein
  Atrans represents the absorbance, as measured by FT-IR spectroscopy (Fourier Transform Infrared Spectroscopy), at a wavenumber at which the N—H stretching vibration absorption signal of the trans-2-alkylcyclohexylamine residue represented by General Formula (a) of the corresponding all-trans amide-based compound appears, and
  Acis represents the absorbance, as measured by FT-IR spectroscopy, at a wavenumber at which the N—H stretching vibration absorption signal of the cis-2-alkylcyclohexylamine residue represented by General Formula (b) of the corresponding all-cis amide-based compound appears.

In the specification and claims, the term "all-trans amide-based compound" or "all-trans compound" means the amide-based compound of General Formula (1) wherein all $R^2$ groups are the same and represent a trans-2-alkylcyclohexylamine residue represented by General Formula (a). Similarly, the term "all-cis amide-based compound" or "all-cis compound" means the amide-based compound of General Formula (1) wherein all $R^2$ groups are the same and represent a cis-2-alkylcyclohexylamine residue represented by General Formula (b).

Item 7. A mixture according to any one of Items 1 to 4, wherein $R^1$ is a 1,2,3,4-butanetetracarboxylic acid residue, and the mixture has a trans 2-alkylcyclohexylamine residue absorbance proportion (Ctrans) of at least 58.8% but less than 71.5% as defined by equation (E):

$$Ctrans(\%) = [Atrans/(Atrans + Acis)] \times 100 \quad (E)$$

wherein
  Atrans represents the absorbance, as measured by FT-IR spectroscopy, at a wavenumber at which the N—H stretching vibration absorption signal of the trans-2-alkylcyclohexylamine residue represented by General Formula (a) of the corresponding all-trans amide-based compound appears, and
  Acis represents the absorbance, as measured by FT-IR spectroscopy, at a wavenumber at which the N—H stretching vibration absorption signal of the cis-2-alkylcyclohexylamine residue represented by General Formula (b) of the corresponding all-cis amide-based compound appears.

Item 8. An amide-based compound represented by General Formula (1):

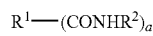

wherein
  a represents an integer of 2 to 6,
  $R^1$ represents a $C_{2-30}$ saturated or unsaturated aliphatic polycarboxylic acid residue, and said aliphatic polycarboxylic acid residue has a valence of 2 to 6 (the same value as a), and
  the two to six $R^2$ groups are the same, and represent a trans-2-alkylcyclohexylamine residue represented by General Formula (a):

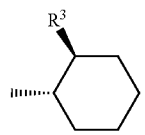

wherein $R^3$ represents a $C_{1-10}$ linear or branched alkyl group (namely, an all-trans amide-based compound).

Item 9. An amide-based compound according to Item 8, wherein $R^3$ is a $C_{1-6}$ linear or branched alkyl group.

Item 10. An amide-based compound according to Item 8, wherein $R^3$ is methyl.

Item 11. An amide-based compound according to any one of Items 8 to 10, wherein $R^1$ is a 1,2,3-propanetricarboxylic acid residue or a 1,2,3,4-butanetetracarboxylic acid residue.

Item 12. An amide-based compound according to Item 8, wherein $R^1$ is a 1,2,3,4-butanetetracarboxylic acid residue and $R^3$ is methyl.

Item 13. An amide-based compound according to Item 8, wherein $R^1$ is a 1,2,3-propanetricarboxylic acid residue and $R^3$ is methyl.

Item 14. A polyolefin resin nucleating agent comprising the mixture according to any one of Items 1 to 7.

Item 15. A polyolefin resin nucleating agent comprising the amide-based compound according to any one of Items 8 to 13.

Item 16. A polyolefin resin composition comprising a polyolefin resin and a mixture according to any one of Items 1 to 7 or an amide-based compound according to any one of Items 8 to 13 (or a polyolefin resin nucleating agent according to Item 14 or 15).

Item 17. A polyolefin resin composition according to Item 16, wherein the composition contains 0.01 to 10 parts by weight of the mixture according to any one of Items 1 to 7 or the amide-based compound according to any one of Items 8 to 13 (or the polyolefin resin nucleating agent according to Item 14 comprising the mixture or the polyolefin resin nucleating agent according to Item 15 comprising the amide-based compound, calculated as the mixture or the amide-based compound), per 100 parts by weight of the polyolefin resin.

Item 18. A polyolefin resin molded product obtainable (or obtained) by molding a polyolefin resin composition according to Item 16 or 17.

Item 19. A process for producing a mixture of amide-based compounds represented by General Formula (1):

(1)

wherein
a represents an integer of 2 to 6, $R^1$ represents a $C_{2-30}$ saturated or unsaturated aliphatic polycarboxylic acid residue, and said aliphatic polycarboxylic acid residue has a valency of 2 to 6 (the same value as a), and the two to six $R^2$ groups are the same or different, and each represent a trans-2-alkylcyclohexylamine residue represented by General Formula (a):

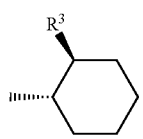
(a)

wherein $R^3$ represents a $C_{1-10}$ linear or branched alkyl group, or a cis-2-alkylcyclohexylamine residue represented by General Formula (b):

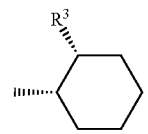
(b)

wherein $R^3$ represents a $C_{1-10}$ linear or branched alkyl group, the trans-2-alkylcyclohexylamine residue represented by General Formula (a) being present in a proportion of at least 70 mole % but less than 100 mole % of the total 2-alkylcyclohexylamine residues in the mixture, the process comprising subjecting, to amidation reaction, a polycarboxylic acid represented by General Formula (2):

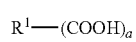
(2)

wherein $R^1$ represents a $C_{2-30}$ saturated or unsaturated aliphatic polycarboxylic acid residue, and a represents an integer of 2 to 6 or a reactive derivative thereof, and an amine mixture of (i) a trans-2-alkylcyclohexylamine represented by General Formula (3a):

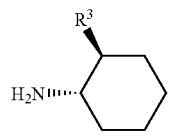
(3a)

wherein $R^3$ represents a $C_{1-10}$ linear or branched alkyl group, and (ii) a cis-2-alkylcyclohexylamine represented by General Formula (3b)

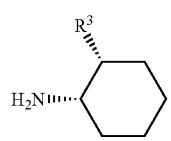
(3b)

wherein $R^3$ represents a $C_{1-10}$ linear or branched alkyl group, the content of the trans-2-alkylcyclohexylamine in the amine mixture being at least 70% but less than 100% as determined by gas chromatography (GLC).

Item 20. A process for producing an amide-based compound (all-trans amide-based compound) represented by General Formula (1):

(1)

wherein
a represents an integer of 2 to 6, $R^1$ represents a $C_{2-30}$ saturated or unsaturated aliphatic polycarboxylic acid residue, and said aliphatic polycarboxylic acid residue has a valency of 2 to 6 (the same value as a), and the two to six $R^2$ groups are the same and represent a trans-2-alkylcyclohexylamine residue represented by General Formula (a):

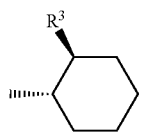

(a)

wherein $R^3$ represents a $C_{1-10}$ linear or branched alkyl group, the process comprising subjecting, to amidation reaction, a polycarboxylic acid represented by General Formula (2):

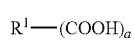

(2)

wherein $R^1$ represents a $C_{2-30}$ saturated or unsaturated aliphatic polycarboxylic acid residue, and a represents an integer of 2 to 6 or a reactive derivative thereof, and a trans-2-alkylcyclohexylamine represented by General Formula (3a):

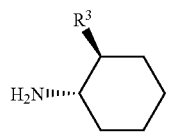

(3a)

wherein $R^3$ represents a $C_{1-10}$ linear or branched alkyl group.

Item 21. A method for improving rigidity of a polyolefin resin molded product, the method comprising incorporating a mixture according to any one of Items 1 to 7 or an amide-based compound according to any one of Items 8 to 13 (or a nucleating agent according to Item 14 or 15) into a polyolefin resin to obtain a polyolefin resin composition, and molding the polyolefin resin composition.

Item 22. Use of a mixture according to any one of Items 1 to 7 or an amide-based compound according to any one of Items 8 to 13 for improving rigidity of a polyolefin resin molded product.

The invention provides a mixture of amide-based compounds or an all-trans amide-based compound useful as a polyolefin resin nucleating agent. The mixture of amide-based compounds or the all-trans amide-based compound is incorporated into a polyolefin resin to give a polyolefin resin composition that can be processed into a molded product with excellent transparency, crystallizability (heat resistance) and rigidity.

The polyolefin resin nucleating agent comprising the mixture of amide-based compounds or the all-trans amide-based compound of the invention has excellent thermal stability and alkali resistance.

DETAILED DESCRIPTION OF THE INVENTION

Amide-based Compound

Figure 1:
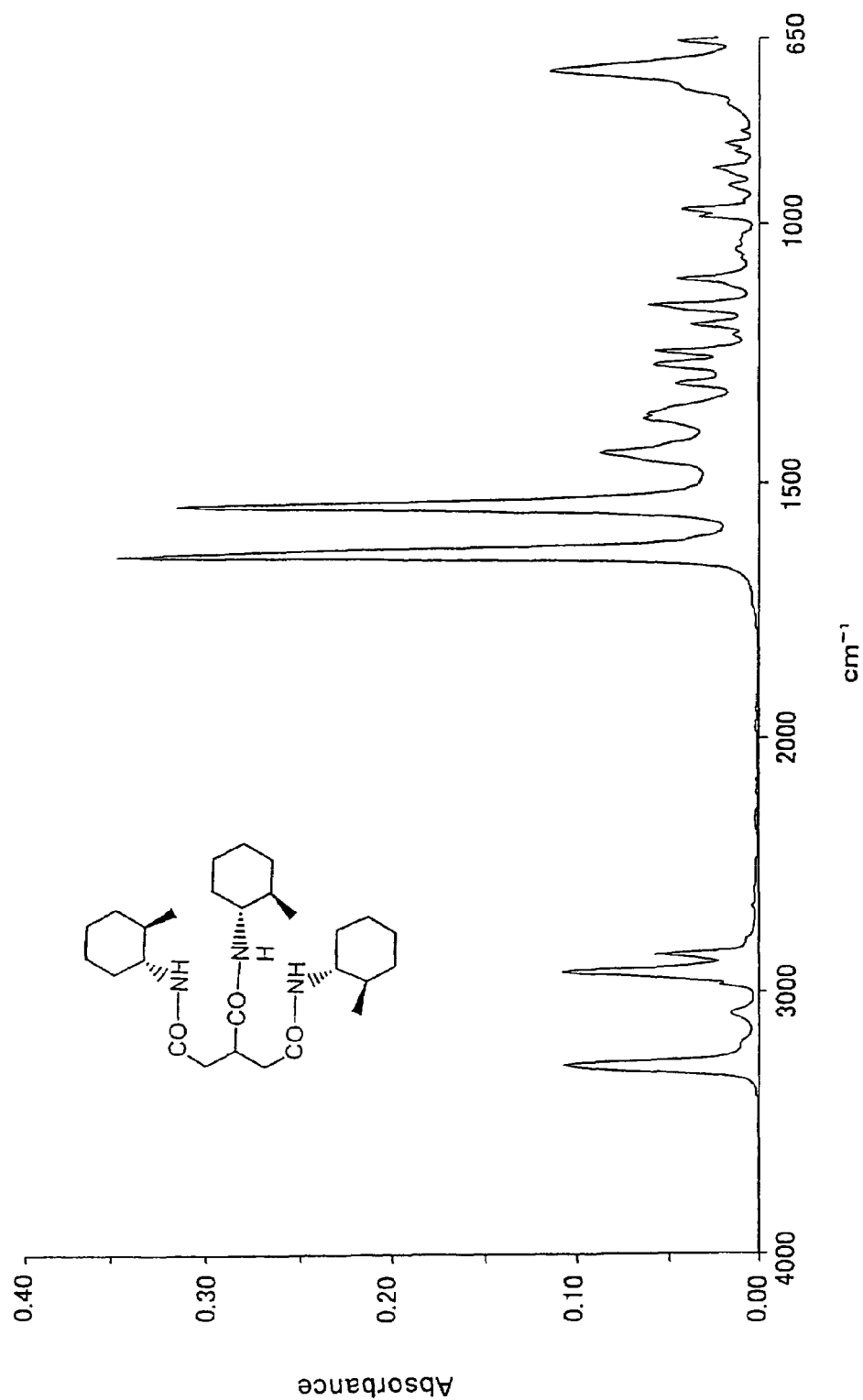
FIG. 1 is an FT-IR chart of 1,2,3-propanetricarboxylic acid tris(trans-2-methylcycloheylamide).

Useful as a polyolefin resin nucleating agent of the invention is an all-trans amide-based compound represented by General Formula (1), or a mixture of two or more amide-based compounds represented by General Formula (1), in which the proportion of the total content of trans structure (trans-2-alkylcyclohexylamine residues of the formula (a)) to the total content of cis structure (cis-2-alkylcyclohexylamine residues of the formula (b)), i.e., total trans structure content/total cis structure content), of the stereoisomeric 2-alkylcyclohexylamine residues is within the range of 70/30 to 100/0.

As described above, the ratio of the trans-configured moiety to cis-configured moiety in the amide-based compound mixture is now found to be substantially the same as the ratio of the trans isomer:cis isomer (as determined by GLC) of the 2-methylcyclohexylamine used as the starting material, based on the results of a series of studies, such as comparison of the trans:cis ratio of the starting 2-alkylcyclohexylamine with the trans:cis ratio of the unreacted 2-alkylcyclohexylamine recovered after subjecting said starting 2-alkylcyclohexylamine to amidation reaction. Thus, the ratio of trans configured moiety:cis configured moiety in the amide-based compound mixture is controllable by the trans:cis isomer ratio of the starting material amine.

Typically, an amide-based compound (a mixture of two or more amide-based compounds or an all-trans amide-based compound) represented by General Formula (1) of the invention includes the following embodiments.

(i) A mixture of amide-based compounds wherein at least one member of the two to six $R^2$ groups represents a trans-2-alkylcyclohexylamine residue of the formula (a) (trans-configured moiety) and the remainder represent a cis-2-alkylcyclohexylamine residue of the formula (b) (cis-configured moiety), wherein the trans-2-alkylcyclohexylamine residue of the formula (a) is present in a proportion of at least 70 mole % but less than 100 mole % of the total 2-alkylcyclohexylamine residues in the mixture.

ii) A mixture of at least one amide-based compound (all-trans compound) wherein all of the two to six $R^2$ groups represent a trans-2-alkylcyclohexylamine residue of the formula (a) (trans-configured moiety), and at least one amide-based compound (all-cis compound) wherein all of the two to six $R^2$ groups represent a cis-2-alkylcyclohexylamine residue of the formula (b) (cis-configured moiety), wherein the trans-2-alkylcyclohexylamine residue of the formula (a) is present in a proportion of at least 70 mole % but less than 100 mole % of the total 2-alkylcyclohexylamine residues in the mixture.

(iii) A composition comprising 1) a mixture of at least two amide-based compounds wherein at least one member of the two to six $R^2$ groups represents a trans-2-alkylcyclohexylamine residue of the formula (a) (trans-configured moiety) and the remainder represent a cis-2-alkylcyclohexylamine residue of the formula (b) (cis-configured moiety), and 2) an all-trans compound, wherein the trans-2-alkylcyclohexylamine residue of the formula (a) is present in a proportion of at least 70 mole % but less than 100 mole % of the total 2-alkylcyclohexylamine residues in the composition.

(iv) A single amide-based compound (namely, all-trans compound) wherein all of the two to six $R^2$ groups represent a trans-2-alkylcyclohexylamine residue of the formula (a) (trans-configured moiety).

The present invention is not limited to the embodiments (i) to (iv) described above, and also include other embodiments, so far as the trans-2-alkylcyclohexylamine residue of the formula (a) is present in a proportion of at least 70 mole % but less than 100 mole % of the total 2-alkylcyclohexylamine residues.

<Preferable Amide-based Compounds>

Preferable among the amide-based compounds of the invention are mixtures wherein the trans-2-alkylcyclohexylamine residue of the formula (a) is present in a proportion of at least 70 mole %, particularly at least 71.9 mole %, but less than 100 mole %, or an all-trans single compound.

Among such mixtures, preferable are mixtures wherein the trans-2-alkylcyclohexylamine residue of the formula (a) is present in a proportion of 70 to 90 mole %, particularly 71.9 to 80 mole %.

In General Formula (1), it is advantageous that $R^3$ is $C_1$ to $C_6$, preferably $C_1$ to $C_4$, linear or branched alkyl, particularly methyl.

Compounds of General Formula (1) wherein a is 3 or 4 are preferable. Among them, compounds in which $R^1$ is 1,2,3,4-butanetetracarboxylic acid (hereinafter referred to as "BTC") residue or 1,2,3-propanetricarboxylic acid (hereinafter referred to as "PTC") residue are preferable.

Particularly, from the standpoint of improving such physical properties as transparency, rigidity, crystallization temperature, thermal stability and alkali resistance, amide-based compounds of General Formula (1) wherein $R^1$ is a 1,2,3,4-butanetetracarboxylic acid residue or a 1,2,3-propanetricarboxylic acid residue, and $R^2$ is a 2-alkyl ($C_1$ to $C_6$, particularly methyl)-cyclohexylamine residue are preferable.

It should be noted that the content (proportion) of the total trans-configured moiety in the amide-based compound mixture or the total content of the trans-configured moiety of the all-trans compound is, as will be described in Examples, linearly proportional to the trans-configured moiety absorbance proportion (Ctrans) calculated from the absorbance (Atrans) as measured by FT-IR spectroscopy, at a wavenumber at which the N—H stretching vibration absorption signal of the corresponding all-trans amide-based compound appears, and the absorbance (Acis), as measured by FT-IR spectroscopy, at a wavenumber at which the N—H stretching vibration absorption signal of the corresponding all-cis amide-based compound appears. Therefore, said content (proportion) is readily verified by measuring the FT-IR spectrum and using a calibration line.

For example, amide-based compound mixtures of the invention, wherein $R^1$ is a 1,2,3-propanetricarboxylic acid residue and the trans-configured moiety is present in a proportion of at least 70 mole % but less than 100 mole %, have a trans 2-alkylcyclohexylamine residue absorbance proportion (Ctrans) of at least 56.3% but less than 72.0% as defined by equation (E):

$$C\text{trans}(\%)=[A\text{trans}/(A\text{trans}+A\text{cis})]\times 100 \tag{E}$$

wherein

Atrans represents the absorbance, as measured by FT-IR spectroscopy (Fourier Transform Infrared Spectroscopy), at a wavenumber at which the N—H stretching vibration absorption of the trans-2-alkylcyclohexylamine residue represented by General Formula (a) of the corresponding all-trans amide-based compound appears, and Acis represents the absorbance, as measured by FT-IR spectroscopy, at a wavenumber at which the N—H stretching vibration absorption of the cis-2-alkylcyclohexylamine residue represented by General Formula (b) of the corresponding all-cis amide-based compound appears.

Preferable amide-based compound mixtures of the invention, wherein $R^1$ is a 1,2,3-propanetricarboxylic acid residue, have a Ctrans value of 56.3 to 61.6%, particularly 57.3 to 61.1%.

All-trans compounds wherein $R^1$ is a 1,2,3-propanetricarboxylic acid residue have a Ctrans value of 72.0%.

Amide-based compound mixtures of the invention, wherein $R^1$ is a 1,2,3,4-butanetetracarboxylic acid residue and the trans-configured moiety is present in a proportion of at least 70 mole % but less than 100 mole %, have a trans 2-alkylcyclohexylamine residue absorbance proportion (Ctrans) of at least 58.8% but less than 71.5% as defined by the above equation (E).

Preferable amide-based compound mixtures of the invention, wherein $R^1$ is a 1,2,3,4-butanetetracarboxylic acid residue, have a Ctrans value of 58.8 to 63.1%, particularly 59.6 to 63.1%.

All-trans compounds wherein $R^1$ is a 1,2,3,4-butanetetracarboxylic acid residue have a Ctrans value of 71.5%.

Preferable among the compounds represented by General Formula (1) and constituting the mixture or all-trans compound of the invention are the following compounds:

1,2,3,4-butanetetracarboxylic acid tetrakis(2-methylcyclohexylamide);
1,2,3,4-butanetetracarboxylic acid tetrakis(2-ethylcyclohexylamide);
1,2,3,4-butanetetracarboxylic acid tetrakis(2-n-propylcyclohexylamide);
1,2,3,4-butanetetracarboxylic acid tetrakis(2-iso-propylcyclohexylamide);
1,2,3,4-butanetetracarboxylic acid tetrakis(2-n-butylcyclohexylamide);
1,2,3,4-butanetetracarboxylic acid tetrakis(2-sec-butylcyclohexylamide);
1,2,3,4-butanetetracarboxylic acid tetrakis(2-iso-butylcyclohexylamide);
1,2,3,4-butanetetracarboxylic acid tetrakis(2-n-pentylcyclohexylamide);
1,2,3,4-butanetetracarboxylic acid tetrakis(2-n-hexylcyclohexylamide);
1,2,3-propanetricarboxylic acid tris(2-methylcyclohexylamide);
1,2,3-propanetricarboxylic acid tris(2-ethylcyclohexylamide);
1,2,3-propanetricarboxylic acid tris(2-n-propylcyclohexylamide);
1,2,3-propanetricarboxylic acid tris(2-iso-propylcyclohexylamide);
1,2,3-propanetricarboxylic acid tris(2-n-butylcyclohexylamide);
1,2,3-propanetricarboxylic acid tris(2-sec-butylcyclohexylamide);
1,2,3-propanetricarboxylic acid tris(2-iso-butylcyclohexylamide);
1,2,3-propanetricarboxylic acid tris(2-n-pentylcyclohexylamide);
1,2,3-propanetricarboxylic acid tris(2-n-hexylcyclohexylamide).

Preferable among the above compounds is an amide-based compound represented by General Formula (1) wherein $R^1$ is 1,2,3,4-butanetetracarboxylic acid residue or 1,2,3-propanetricarboxylic acid residue and $R^2$ is 2-methylcyclohexylamine residue.

Process for Producing the Amide-based Compounds

The amide-based compounds of the invention can be produced in various ways. In general, however, the compounds are produced by reacting an aliphatic polycarboxylic acid having 2 to 6 carboxyl groups, or a reactive derivative thereof (for example, acid anhydride, acid halide, lower alkyl ester) with a 2-alkylcyclohexylamine (with trans isomer content of 70% or more as determined by GLC (%)) represented by General Formula $R^2NH_2$ (wherein $R^2$ are as defined above). As a reactive derivative, a lower alkyl ($C_1$ to $C_4$, especially $C_1$) ester is easy to handle and therefore preferable.

More specifically, the process for producing an amine-based compound mixture of the invention comprises amidating a polycarboxylic acid represented by General Formula (2), or a reactive derivative thereof, with an amine mixture of a trans-2-alkylcyclohexylamine represented by the foregoing General Formula (3a) and a cis-2-alkylcyclohexylamine represented by the foregoing General Formula (3b) and having a trans-2-alkylcyclohexylamine content of 70% or more but less than 100% as measured by GLC.

A process for preparing an all-trans amide-based compound of the invention is characterized by subjecting a polycarboxylic acid of General Formula (2) or a reactive derivative thereof and a trans-2-alkylcyclohexylamine represented by the foregoing General Formula (3a) to amidation reaction.

<Polycarboxylic Acid>

The above-described polycarboxylic acid is represented by General Formula (2):

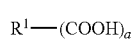
(2)

wherein $R^1$ represents a $C_{2-30}$ saturated or unsaturated aliphatic polycarboxylic acid residue, and a represents an integer of 2 to 6.

Thus, the "polycarboxylic-acid residue" represented by $R^1$ of General Formula (1) denotes a residue obtained by removing all of the carboxyl groups from the aliphatic polycarboxylic acid represented by General Formula (2), and is a residue with the same valence number as a, i.e., a group with a valency of 2 to 6. The number of carbon atoms of $R^1$ refers to the number of carbon atoms contained in the polycarboxylic acid residue obtained by removing all of the carboxyl groups.

Examples of polycarboxylic acids usable in the invention include a saturated or unsaturated aliphatic polycarboxylic acid represented by General Formula (2). The polycarboxylic acid may have one or more (particularly, 1 or 2) substituents selected from the group consisting of hydroxyl, alkyl ($C_1$ to $C_{10}$, preferably $C_1$ to $C_4$), alkenyl ($C_2$ to $C_{10}$, preferably $C_3$ or $C_4$), aryl ($C_6$ to $C_{20}$, preferably $C_6$ to $C_{15}$) and acetoxy.

Examples of the aliphatic polycarboxylic acids include a saturated or unsaturated polycarboxylic acid in which $R^1$ in General Formula (2) has 2 to 30 carbon atoms, preferably 3 to 10 carbon atoms, and the number of carboxyl groups is 2 to 6 (particularly, 3 or 4). Examples thereof include diphenylmalonic acid, succinic acid, phenylsuccinic acid, diphenylsuccinic acid, glutaric acid, 3,3-dimethylglutaric acid, adipic acid, pimelic acid, suberic acid, azelaic acid, sebacic acid, 1,12-dodecanedioic acid, 1,14-tetradecanedioic acid, 1,18-octadecanedioic acid, citric acid, methanetricarboxylic acid, ethanetricarboxylic acid, propanetricarboxylic acid, propenetricarboxylic acid, camphoronic acid, butanetricarboxylic acid, pentanetricarboxylic acid, hexanetricarboxylic acid, heptanetricarboxylic acid, octanetricarboxylic acid, nonanetricarboxylic acid, decanetricarboxylic acid, acetoxy-propanetricarboxylic acid, acetoxy-pentanetricarboxylic acid, acetoxy-heptanetricarboxylic acid, ethanetetracarboxylic acid, propanetetracarboxylic acid, butanetetracarboxylic acid, pentanetetracarboxylic acid, dodecanetetracarboxylic acid, pentanepentacarboxylic acid, acetoxy-pentanepentacarboxylic acid, pentanehexacarboxylic acid, tetradecanehexacarboxylic acid, ethylenediamine-tetraacetic acid, nitrilotriacetic acid, ethylene glycol bis(β-aminoethyl ether) N,N,N',N'-tetraacetic acid, diethylenetriamine-pentaacetic acid, N-hydroxyethyl-ethylenediamine-N,N',N'-triacetic acid, 1,3-diaminopropane-2-ol-N,N,N',N'-tetraacetic acid, 1,2-diaminopropane-N,N,N',N'-tetraacetic acid, triethylenetetramine-hexaacetic acid, nitrilotripropionic acid, 1,6-hexamethylenediamine-tetraacetic acid, N-(2-carboxyethyl)iminodiacetic acid, etc.

<2-alkylcyclohexylamine>

The 2-alkylcyclohexylamine residue represented by $R^2$ of General Formula (1) denotes a residue obtained by removing the amino group from a trans-2-alkyl-cyclohexylamine represented by General Formula (3a):

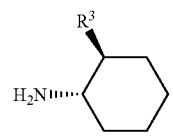
(3a)

wherein $R^3$ represents a $C_{1-10}$ linear or branched alkyl group, or from a cis-2-alkylcyclohexylamine represented by General Formula (3b):

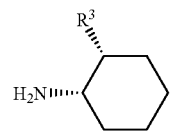
(3b)

wherein $R^3$ represents a $C_{1-10}$ linear or branched alkyl group.

Examples of such 2-alkylcyclohexylamine are cis isomer, trans isomer, or a mixture thereof, of a 2-alkylcyclohexylamine wherein the alkyl moiety is a linear or branched alkyl group ($C_1$ to $C_{10}$), such as 2-methylcyclohexylamine, 2-ethylcyclohexylamine, 2-n-propylcyclohexylamine, 2-iso-propylcyclohexylamine, 2-n-butylcyclohexylamine, 2-iso-butylcyclohexylamine, 2-sec-butylcyclohexylamine, 2-tert-butylcyclohexylamine, 2-n-pentylcyclohexylamine, 2-n-hexylcyclohexylamine, 2-n-heptylcyclohexylamine, 2-n-octylcyclohexylamine, 2-ethylhexylcyclohexylamine, 2-n-nonylcyclohexylamine, 2-n-decylcyclohexylamine, etc.

Preferable among these are cis- or trans-2-alkyl ($C_1$ to $C_5$) cyclohexylamines or a mixture thereof, and specific examples include 2-methylcyclohexylamine, 2-ethylcyclohexylamine, 2-n-propylcyclohexylamine, 2-iso-propylcyclohexylamine, 2-n-butylcyclohexylamine, 2-iso-butylcyclohexylamine, 2-sec-butylcyclohexylamine, 2-tert-butylcyclohexylamine, 2-n-pentylcyclohexylamine, etc., and in particular, cis- or trans-2-methylcyclohexylamine or a mixture thereof is preferable.

Such amines can be used singly or in a suitable combination of two or more for the amidation reaction. The purity of these amines (trans isomer, cis isomer, or a mixture of trans isomer and cis isomer) may be 100%, but a small amount of impurities may be contained therein. The purity of 2-alkyl-cyclohexylamines is generally 98% by weight or more, preferably 99% by weight or more, and more preferably 99.5% by weight or more.

As described above, the proportion of total content of trans structure:total content of cis structure (total trans structure content/total cis structure content) of the stereoisomeric 2-alkyl ($C_1$ to $C_{10}$)-cyclohexylamine residue constituting the amide-based compound mixture or all-trans compound is 70/30 to 100/0.

In other words, the invention includes a single amide-based compound of General Formula (1) wherein all of the two to six $R^2$ groups in the amide-based compound represented by General Formula (1) are trans. The invention also include a mixture of at least two amide-based compounds of the formula (1) wherein the trans-configured moiety is present in a proportion of at least 70 mole % but less than 100 mole % of the total 2-alkylcyclohexylamine residues in the mixture.

Therefore, in preparing such an all-trans amide-based compound or a mixture having a trans-configured moiety proportion of not less than 70 mole % but less than 100 mole %, it is preferable to use, as a starting material, a trans-2-alkylcyclohexylamine (i.e, trans isomer itself), or a mixture in which a trans-2-alkylcyclohexylamine (trans isomer) and a cis-2-alkylcyclohexylamine (cis isomer) are contained and in which the content of the trans-2-alkylcyclohexylamine (measured by GLC) is 70% or more, particularly 71.9% or more, preferably 70 to 90%, and more preferably 70 to 80%. The trans-2-alkylcyclohexylamine content (measured by GLC) is preferably 70 to 80% from the standpoint of availability and economy.

Such a pure trans isomer or a trans-isomer-rich mixture is obtained by a procedure used for isolating the trans isomer alone by, for example, distillation etc., from a commercially available mixture of the trans isomer and cis isomer (the trans isomer content measured by GLC is about 68.4%). The distillation may be carried out under atmospheric pressure or reduced pressure. From the standpoint of suppressing decomposition of the amine, the distillation is preferably carried out under a reduced pressure. The distillation temperature is not particularly limited, but is 150° C. or lower, and preferably 100° C. or lower. When the distillation is conducted under reduced pressure, the pressure is not particularly limited, but it is preferably about 0.5 to about 15 kPa, and more preferably about 1 to about 10 kPa. Distillation can be conducted by a conventional method, and for example, include, but is not limited to, a simple distillation, a distillation using a multi-stage distillation column, etc. Such distillation makes it possible to obtain substantially pure trans isomer alone, or to obtain a trans isomer-cis isomer mixture with a trans isomer content of 70% or more (measured by GLC).

The amine starting material, which is the thus-obtained pure trans isomer or a trans isomer-cis isomer mixture with a trans isomer content of 70% or more (measured by GLC), and a polycarboxylic acid represented by General Formula (2) or a reactive derivative thereof (for example, acid anhydride, acid halide, ester, etc.), are subjected to amidation reaction to thereby synthesize the desired amide-based compound represented by General Formula (1) or the desired mixture.

The desired mixture of the amide-based compounds represented by General Formula (1) may also be produced by mixing an all-trans amide-based compound obtained by the above process wherein the $R^2$ groups are 100% in trans configuration with an amide-based compound having different type of a stereoisomeric configuration (for example, an amide-based compound wherein the two to six $R^2$ groups in the molecule are all in cis configuration, mixed-type amide-based compounds wherein at least one member of the two to six $R^2$ groups has a trans configuration, and the remainder have a cis configuration, etc.) such that the proportion of the trans-2-alkylcyclohexylamine residue represented by formula (a) is 70 mole % or more but less than 100 mole %.

The above-mentioned amidation reaction can be conducted according to known processes, for example, by the processes disclosed in Japanese Unexamined Patent Publication No. 1995-242610. More specifically, the following process may be adopted.

(i) A polycarboxylic acid represented by General Formula (2) is reacted with 3 to 20 equivalents of the amine starting material at 60 to 280° C. in an inert solvent for 2 to 50 hours.

In this production process, it is preferable to use an activator so as to shorten the reaction time. Examples of the activators include phosphorus pentoxide, polyphosphoric acid, phosphorus pentoxide-methanesulfonic acid, phosphites (e.g., triphenyl phosphite)-pyridine, phosphite-metal salts (for example, lithium chloride etc.), triphenylphosphine-hexachloroethane, etc. In general, an activator is used in approximately equimolar amount relative to each carboxyl group of the polycarboxylic acid represented by General Formula (2).

(ii) A chloride of the polycarboxylic acid represented by General Formula (2) is reacted with 3 to 6 equivalents of the amine starting material at 0 to 100° C. in an inert solvent for 1 to 5 hours.

(iii) A polyalkyl ester of a polycarboxylic acid represented by General Formula (2) is reacted with 3 to 30 equivalents of the amine starting material at 20 to 280° C. in the absence of a solvent or in an inert solvent, and in the absence or absence of a catalyst for 3 to 50 hours.

Examples of such catalysts include acid catalysts, base catalysts, etc. that are generally used for usual ester-amide interchange reactions, with the base catalysts being more preferable. Specific examples thereof include alkali metals and alkali metal hydrides, such as Li, Na, K, LiH, NaH, KH, etc., metal hydroxides, such as LiOH, NaOH, KOH, etc., metal alcoholates, such as NaOMe, NaOEt, tert-BuOK, etc., alkali metal amides, such as $NaNH_2$, $LiNPr_2$, etc. In general, such catalysts are used in substantially equimolar quantity relative to each carboxyl group of the polycarboxylic acid.

Examples of inert solvents usable in methods (i), (ii) and (iii) described above include benzene, toluene, xylene, chloroform, chlorobenzene, dichlorobenzene, tetrahydrofuran, dioxane, acetonitrile, N,N-dimethylformamide, N,N-dimethylacetamide, N-methylpyrolidone, etc.

Polyolefin Resin Nucleating Agent

The polyolefin resin nucleating agent of the invention consists of a mixture of amide-based compounds represented by General Formula (1) or an all-trans compound of the invention, or comprises a mixture of amide-based compounds or an all-trans compound of the invention together with the additives, polyolefin resin modifiers, etc. that will be mentioned below.

The particle diameter of the amide-based compound that is used as a polyolefin resin nucleating agent is not limited as long as the effects of the invention can be obtained. However, from the viewpoint of dispersibility or dissolution speed in a molten resin, the smaller the average particle diameter the better. The average particle diameter, as measured by a laser diffraction light scattering method, is generally 0.1 to 500 µm, preferably 1 to 200 µm, and more preferably 1 to 100 µm.

The crystalline form of the amide-based compound of the invention is not limited as long as the effects of the invention can be attained, and any crystal forms, such as cubic, monoclinic, trigonal, hexagonal, etc., can be used.

There is no particular restriction on the particle diameter of the crystals and it can be suitably selected depending on the purposes. For example, when it is intended to shorten the time for dispersing, dissolving or melting the amide-based compound into a polyolefin resin, the maximum particle diameter is preferably not more than 50 µm and more preferably not more than 10 µm, depending on the temperature for dispersion, dissolution or melting.

Examples of methods for controlling the maximum particle diameter of the amide-based compound within the above ranges include a method comprising pulverizing the amide-based compound into fine particles using conventional apparatus known in the art, and then classifying the obtained fine particles. Specifically, the amide-based compound can be pulverized into fine particles and classified using a jet mill, such as "Fluidized bed counter-jet mill 100AFG" (product name, product of Hosokawa Micron Corporation), "Supersonic jet mill PJM-200" (product name, product of Nippon Pneumatic MFG Co., Ltd.), etc.

If desired, the nucleating agent of the invention may contain compounds that can increase the crystallization temperature of a polyolefin resin composition and/or transparency, as an additive, in addition to the amide-based compound of the invention, insofar as the effects of the invention are not adversely affected. Specific examples of such additives include aromatic carboxylic acid metal salts, aromatic carboxylic acid anhydrides, metal salts of aromatic phosphates, amine salts of aromatic phosphates, sorbitol derivatives, aliphatic dicarboxylic acid metal or amine salts, rosin acid derivatives, hydrogenated nadic acid metal salts, etc.

More specifically, there may be mentioned aromatic carboxylic acid metal salts, such as sodium benzoate, sodium p-tert-butylbenzoate, aluminium hydroxy-bis(p-tert-butylbenzoic acid), etc.; anhydrides of aromatic-carboxylic acids, such as benzoic acid, p-tert-butylbenzoic acid, alkyl-substituted benzoic acids, etc.; metal salts of aromatic phosphates, such as sodium 2,2'-methylene-bis(4,6-di-t-butylphenyl)phosphate, sodium 2,2'-ethylidene-bis(4,6-di-t-butylphenyl)phosphate, lithium 2,2'-methylene-bis(4,6-di-t-butylphenyl)phosphate, lithium 2,2'-ethylidene-bis(4,6-di-t-butylphenyl)phosphate, sodium 2,2'-ethylidene-bis(4-isopropyl-6-t-butylphenyl)phosphate, lithium 2,2'-methylene-bis(4-methyl-6-t-butylphenyl)phosphate, lithium 2,2'-methylene-bis(4-ethyl-6-t-butylphenyl)phosphate, etc.; amine salts of aromatic phosphates such as a salt of 2,2'-methylenebis(4,6-di-tert-butyl phenyl)phosphate with an aliphatic polyamine, etc.; sorbitol derivatives, such as dibenzylidene sorbitol, bis(p-methylbenzylidene)sorbitol, bis(p-ethylbenzylidene)sorbitol, bis(3,4-dimethylbenzylidene)sorbitol, etc.; rosin acid metal salts such as rosin acid sodium salt, rosin acid potassium salt, rosin acid magnesium salt, etc.; metal salts of hydrogenated nadic acid such as disodium hydrogenated nadic acid, etc. Such compounds can be used singly or in combination.

The polyolefin nucleating agent of the invention may further contain known polyolefin modifiers, as optional components. Examples of such polyolefin modifiers include the various additives listed in "The Tables of Positive Lists of Additives" edited by the Japan Hygienic Olefin and Styrene Plastic Association (January, 2002). More specific examples include stabilizers (such as metal compounds, epoxy compounds, nitrogen compounds, phosphorus compounds, sulfur compounds, etc.), UV absorbers (such as benzophenone compounds and benzotriazole compounds), antioxidants (such as phenol compounds, phosphorous ester compounds, and sulfur compounds), surfactants, lubricants (such as paraffin, wax, and other aliphatic hydrocarbons, $C_8$ to $C_{22}$ higher fatty acids, $C_8$ to $C_{22}$ higher fatty acid metal (Li, Na, K, Al, Ca, Mg, Zn) salts, $C_8$ to $C_{22}$ higher aliphatic alcohols, polyglycols, esters of $C_4$ to $C_{22}$ higher fatty acids and $C_4$ to $C_{18}$ aliphatic monohydric alcohols, $C_8$ to $C_{22}$ higher fatty acid amides, silicone oils, and rosin derivatives, fillers (such as talc, hydrotalcite, mica, zeolite, perlite, diatomaceous earth, calcium carbonate, and glass fibers), foaming agents, foaming auxiliaries, polymer additives, plasticizers (such as dialkyl phthalates and dialkyl hexahydrophthalates, etc.), crosslinking agents, crosslinking accelerators, antistatic agents, flame retardants, dispersants, organic and inorganic pigments, working auxiliaries, other nucleating agents, and like additives.

When the above-mentioned additives and/or polyolefin modifiers are used, these may be added to the single amide-based compound represented by General Formula (1), or to a mixture of two or more such compounds, by a known method such as dry blending.

Polyolefin Resin Composition

The polyolefin resin composition of the invention is obtained by incorporating the amide-based compound mixture or all-trans compound of the invention, or a nucleating agent containing the amide-based compound mixture or all-trans compound of the invention, into a polyolefin resin by a conventional method.

The polyolefin resin composition of the invention can be manufactured by any conventional method, with no particular restrictions thereon, as long as the desired resin composition is obtained. For example, a polyolefin resin (powder or granules), the amide-based compound of the invention, and, if necessary, the above-mentioned polyolefin modifier are mixed using a conventional mixer, such as a Henschel mixer, a ribbon blender, a V-blender or the like to obtain a blend type polyolefin resin composition. Other examples include a method in which this blend type polyolefin resin composition is melt-kneaded in a conventional kneader, such as a single screw or twin screw extruder, generally at a temperature of 160 to 300° C., preferably 180 to 260° C., and the extruded strands are cooled, and the strands thus obtained are cut into pellets.

When an amide-based compound mixture of the invention or an all-trans amide-based compound is added, as such, or in the form of a nucleating agent containing the above additives, polyolefin modifier, etc., to a polyolefin resin, there are no particular restrictions on the amount of the mixture or all-trans amide-based compound of the invention (if it is added in the form of such a nucleating agent, the amount calculated as the mixture or all-trans amide-based compound of the invention) as long as the desired effects can be produced, and the amount can be suitably selected from a wide range. Generally, however, the amount is 0.01 to 10 parts by weight, preferably 0.03 to 5 parts by weight, and more preferably 0.05 to 3 parts by weight, per 100 parts by weight of polyolefin resin. By blending the amide-based compound of the invention in an amount within these ranges, effects of the invention can be sufficiently produced.

If the amount is less than 0.01 part by weight, the nucleating agent effect is insufficient and the mechanical characteristics (such as rigidity, etc.) of the molded product are unsatisfactory. In contrast, even if the content exceeds 10 parts by weight, further improved effects are not obtained.

A single-step addition using a conventionally used equipment, such as a single screw or twin screw extruder, etc., is preferable as the method of adding the amide-based compound to the polyolefin resin. However, a two-step addition using a master batch of high concentration in the range of about 2 to 15 wt. % may also be employed.

Examples of polyolefin resins that can be used in the invention include polyethylene-based resins, polypropylene-based resins, polybutene-based resins, methyl-pentene-based resins, butadiene-based resins and the like. Specific examples thereof include high-density polyethylenes, medium-density polyethylenes, linear polyethylenes, ethylene copolymers with an ethylene content of at least 50 wt %, and preferably 70 wt % or higher, propylene homopolymers, propylene copolymers with a propylene content of at least 50 wt %, and preferably 70 wt % or higher, butene homopolymers, butene copolymers with a butene content of at least 50 wt %, and preferably 70 wt % or higher, methyl-pentene homopolymers, methyl-pentene copolymers with a methyl-pentene content of at least 50 wt %, and preferably 70 wt % or higher, polybutadiene, etc.

The above copolymers may be random copolymers or block copolymers. The stereoregularity of these resins may be isotactic or syndiotactic.

Specific examples of comonomers which can form the above various copolymers include ethylene, propylene, butene, pentene, hexene, heptene, octene, nonene, decene, undecene, dodecene and like $C_2$-$C_{12}$ α-olefins; 1,4-endomethylenecyclohexene and like bicyclo-type monomers; methyl (meth)acrylate, ethyl (meth)acrylate and like (meth)acrylic esters; vinyl acetate, etc.

Examples of catalysts used for manufacturing such polymers include not only generally used Ziegler-Natta catalysts but also catalyst systems comprising a combination of a transition metal compound (e.g., a titanium halide such as titanium trichloride or titanium tetrachloride) supported on a support comprising, as a main component, magnesium chloride or like magnesium halides, with an alkyl aluminum compound (such as triethyl aluminum or diethyl aluminum chloride), and metallocene catalysts.

The recommended melt flow rate (hereinafter referred to as "MFR", measured according to JIS K 7210-1995) of the polyolefin resin used in the invention can be suitably selected according to the molding method to be employed, but is usually 0.01 to 200 g/10 minutes, and preferably 0.05 to 100 g/10 minutes.

To the extent that the effect of the invention is not impaired, the above-mentioned known polyolefin modifiers may be added to the polyolefin resin composition of the invention depending on the purpose and/or application thereof.

Polyolefin Resin Molded Article and Method for Improving Rigidity of Molded Article The polyolefin resin molded article of the invention is obtained by molding the polyolefin resin composition of the invention according to a conventional molding method.

Any known method, such as injection molding, extrusion molding, blow molding, pressure forming, rotational molding, or film forming, can be employed as the method for molding the polyolefin resin composition of the invention. The processing conditions may be suitably selected from the wide range of conditions that have been employed to date.

As is clear from the Examples to be described below, the polyolefin resin molded articles obtained in the invention have excellent rigidity. Therefore, the invention provides a method for improving rigidity of polyolefin resin molded articles, the method being characterized by incorporating an all-trans compound or a mixture of two or more compounds represented by General Formula (1) of the invention, or the nucleating agent of the invention, into a polyolefin resin to obtain a resin composition and molding the resin composition.

The thus-obtained polyolefin resin molded articles of the invention can be suitably used in the fields in which polyolefin resin compositions, containing metal phosphates, metal carboxylates, benzylidene sorbitols, etc., as nucleating agents, have been used. Specific examples include medical instruments sterilized by heat, radiation or the like, such as disposable syringes, infusion and transfusion sets, blood collection equipment, etc.; packaging materials for foods, plants, etc., sterilized by radiation or the like; cases such as cases for clothing, containers for storing clothing, etc.; cups for heat-packaging foods, packaging containers for retort-processed foods; containers for use in microwave ovens, cans, bottles, etc., for beverages, such as juice, tea, etc., for cosmetics, medicines, shampoos, etc.; containers and caps for seasonings such as miso, soy sauce, etc.; cases and containers for food stuff such as water, rice, bread, pickles, etc.; sundries such as cases for use in refrigerators, etc.; stationeries; electric and mechanical parts; automobile parts, etc.

EXAMPLES

The invention is described below in detail with reference to examples and comparative examples, but the invention is not limited to these examples.

The melting point of the amide-based compound, which is the nucleating agent for the polyolefin resin of the invention, the content of trans-2-alkylcyclohexylamine residue, the haze value (%) of the polyolefin resin molded article, crystallization temperature (° C.), and flexural modulus (kg/mm$^2$) thermal stability (10% weight reduction temperature, ° C.) and alkali resistance were measured and evaluated by the following methods.

1) Melting Point (° C.)

This was measured using a differential scanning calorimeter (trade name "DSC-50", made by Shimadzu Corp). The temperature of the peak maximum of the endothermic peak was defined as the melting point.

Nitrogen flow rate: 30 ml/minute, heating rate: 10° C./minute, weight of sample: 5 mg, and standard sample: silica gel (5 mg).

2) trans-2-alkylcyclohexylamine Residue Absorbance Proportion (Ctrans)

Using FT-IR spectrometer (product name: "Spectrum One" manufactured by Perkin Elmer, Inc.), the absorption band of the N—H stretching vibrations present at 3400 to 3100 cm$^{-1}$ were measured.

The trans-2-alkylcyclohexylamine residue absorbance proportion (Ctrans) was calculated from the absorbance (Atrans) measured at a wavenumber at which the N—H stretching vibration absorption of the trans-2-alkylcyclohexylamine residue represented by General Formula (a) of the corresponding all-trans amide-based compound appears, and the absorbance (Acis) measured at a wavenumber at which the N—H stretching vibration absorption of the cis-2-alkylcyclohexylamine residue represented by General Formula (b) of the corresponding all-cis amide-based compound appears, according to the equation (E):

$$C trans(\%) = [A trans/(A trans + A cis)] \times 100 \quad (E)$$

wherein

A trans represents the absorbance, as measured by FT-IR spectroscopy, at a wavenumber at which the N—H stretching vibration absorption of the trans-2-alkylcyclohexylamine residue represented by General Formula (a) of the corresponding all-trans amide-based compound appears, and A cis represents the absorbance, as measured by FT-IR spectroscopy, at a wavenumber at which the N—H stretching vibration absorption of the cis-2-alkylcyclohexylamine residue represented by General Formula (b) of the corresponding all-cis amide-based compound appears.

The method will be described below in detail with respect to the trans-2-methylcyclohexylamine residue absorbance proportion (Ctrans, %) of 1,2,3-propanetricarboxylic acid tris (2-methylcyclohexamide).

a) Preparation of Standard Samples 1,2,3-Propanetricarboxylic acid tris(trans-2-methylcyclohexylamide) (all-trans compound) and 1,2,3-propanetricarboxylic acid tris(cis-2-methylcyclohexylamide) (all-cis compound) were fully washed with isopropyl alcohol and an aqueous solution of isopropyl alcohol and dried at 80° C. for 6 hours.

Samples were prepared by mixing the washed and dried 1,2,3-propanetricarboxylic acid tris(trans-2-methylcyclohexylamide) and the washed and dried 1,2,3-propanetricarboxylic acid tris(cis-2-methylcyclohexylamide) such that the mixtures had a trans-2-methylcyclohexylamine residue content of 80 mole %, 50 mole % and 20 mole %, based on the total 2-methylcyclohexylamine residues in the mixture. The washed and dried all-trans compound was used as a sample having a trans-2-methylcyclohexylamine residue content of 100 mole %.

Prior to the FT-IR measurement, each sample thus provided was fully ground using an a gate mortar in the presence of methanol for wetting the sample, and then dried, and then used as a standard sample for FT-IR measurement.

b) Measurement and Preparation of Calibration Line

An FT-IR instrument (Product name "Spectrum One", manufactured by Perkin Elmer, Inc.), equipped with an attenuated total reflection (hereinafter "ATR") accessory (Universal ATR, manufactured by Perkin Elmer, Inc.), was used. The measurement was carried out in the wavenumber range of 650 to 4000 $cm^{-1}$ under the following conditions: resolution=4 $cm^{-1}$, scanning=16 times, and temperature=25° C. Under the conditions, infrared spectra of standard samples having trans-2-methylcyclohexylamine residue contents of 100 mole %, 80 mole %, 50 mole % and 20 mole % were measured by FT-IR-ATR spectroscopy.

Figure 2:
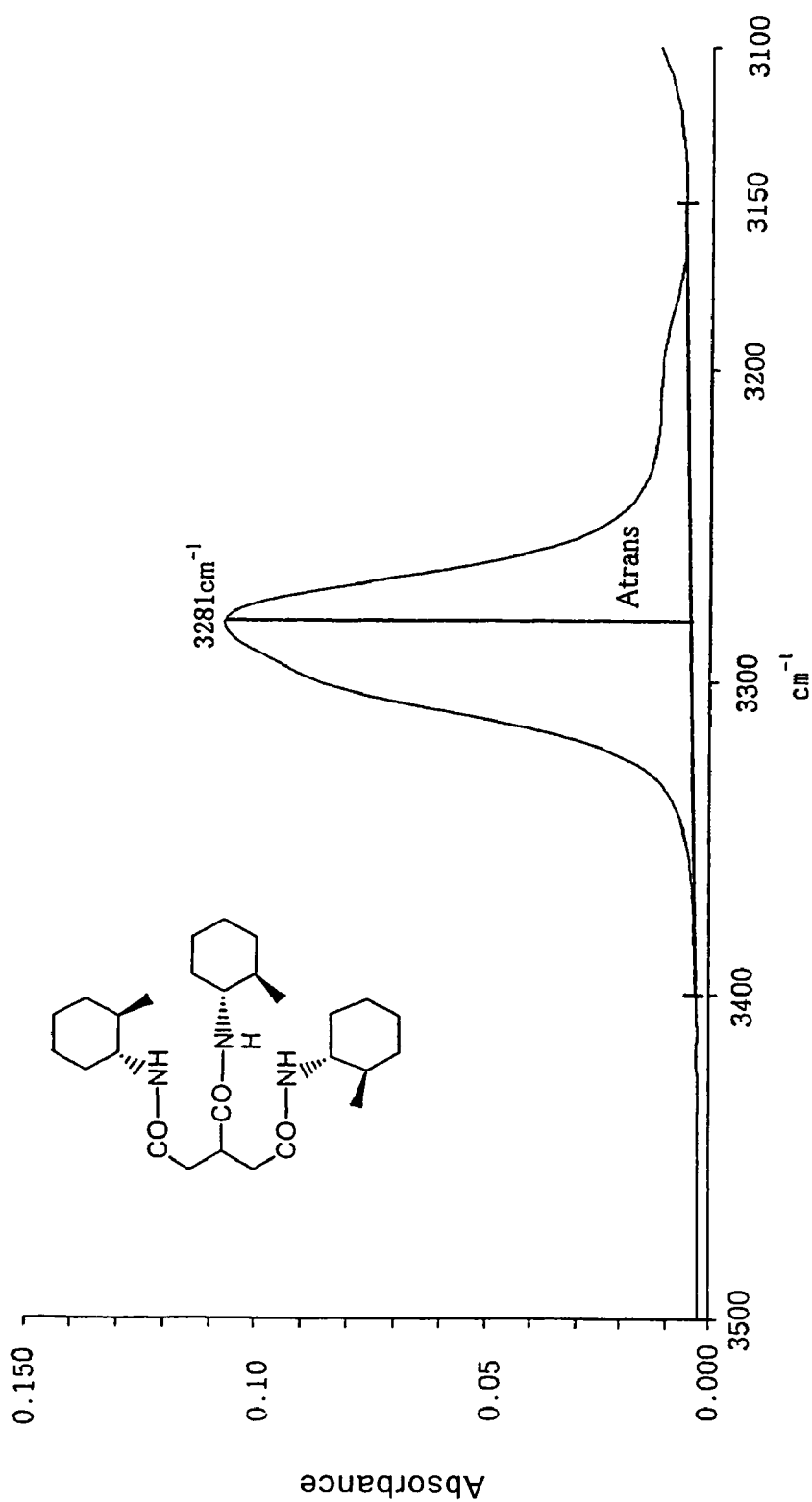
FIG. 2 is an FT-IR chart (3100 to 3500 cm$^{-1}$) of 1,2,3-propanetricarboxylic acid tris(trans-2-methylcycloheylamide).
Figure 3:
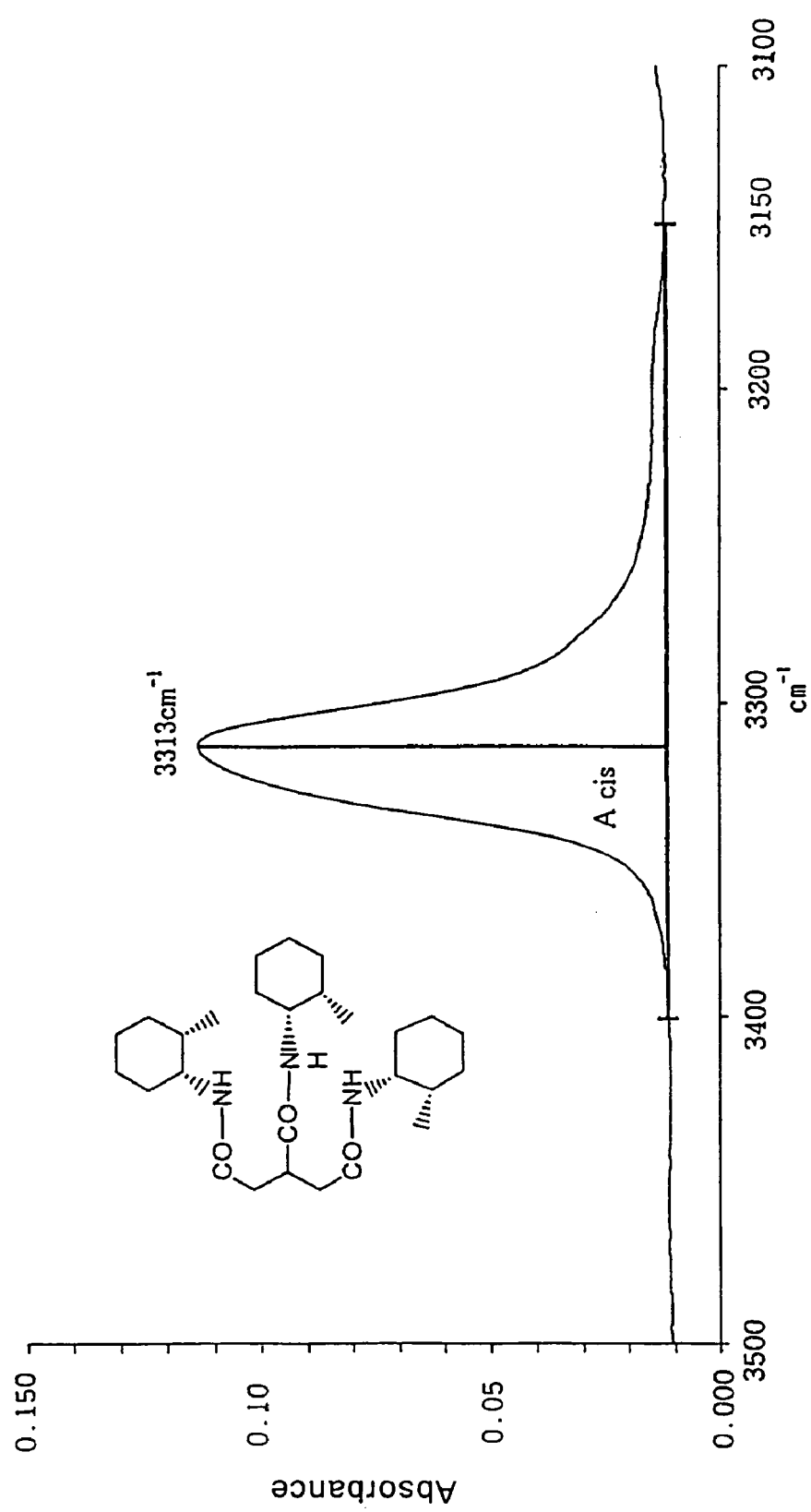
FIG. 3 is an FT-IR chart (3100 to 3500 cm$^{-1}$) of 1,2,3-propanetricarboxylic acid tris(cis-2-methylcycloheylamide).

FIGS. 1 and 2 are the infrared spectrum charts of the all-trans compound. FIG. 3 is the infrared spectrum chart of the corresponding all-cis compound, and FIG. 4 is the infrared spectrum chart of the standard sample having a trans-2-methylcyclohexylamine residue content of 80 mole %.

From the charts as shown in FIGS. 2 and 3 were determined the wavenumber (3281 $cm^{-1}$) at which the N—H stretching vibration absorption signal of trans-2-methylcyclohexylamine residue of the all-trans compound appeared, and the wavenumber (3313 $cm^{-1}$) at which the N—H stretching vibration absorption signal of cis-2-methylcyclohexylamine residue of the all-cis compound appeared.

Figure 4:
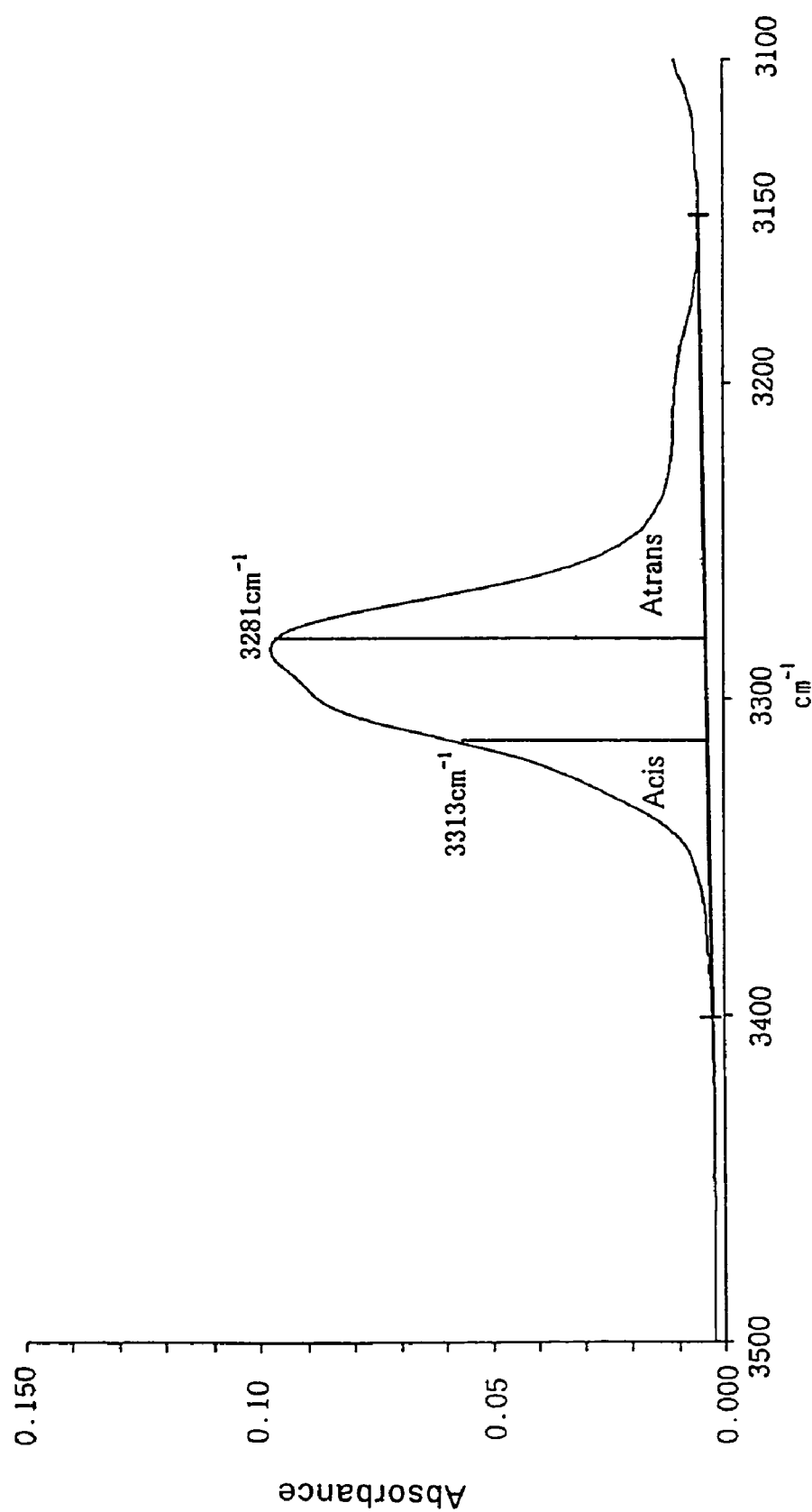
FIG. 4 is an FT-IR chart (3100 to 3500 cm$^{-1}$) of a mixture of 1,2,3-propanetricarboxylic acid tris(trans-2-methylcycloheylamide) and 1,2,3-propanetricarboxylic acid tris(cis-2-methylcycloheylamide) (trans:cis molar ratio=80:20).

Thereafter, as shown in FIG. 4, using the base-line method (3400 $cm^{-1}$, 3150 $cm^{-1}$), the absorbance (Atrans) at 3281 $cm^{-1}$ and the absorbance (Acis) at 3313 $cm^{-1}$ were measured.

Ctrans values (%), namely, [Atrans/(Atrans+Acis)]×100, were plotted against the trans-2-methylcylcohexylamine residue contents (mole %) of the standard samples, whereby a calibration line showing a linearly proportional relation was obtained. From the calibration line, Ctrans values of the mixtures and all-trans amide-based compounds used in Examples and Comparative Examples were determined.

3) Haze Value (%)

The haze value was measured using a haze meter (made by Toyo Seiki Seisakusho) according to JIS K-7136-2000. The smaller the measured value, the higher the transparency.

4) Crystallization Temperature Tc (° C.)

Crystallization temperature was measured using a differential scanning calorimeter (product name: "DSC7" manufactured by Perkin Elmer, Inc.) according to JIS K-7121. The higher the crystallization temperature Tc, the faster the crystallization speed, and therefore the shorter the molding cycle can be.

5) Flexural Modulus ($kg/mm^2$)

Flexural modulus was measured using an Instron universal tester according to JIS K-7203-1982. The test temperature was 25° C. and the test speed was 10 mm/minute. The greater the flexural modulus, the higher the rigidity of the tested sample.

6) Thermal Stability: 10% Weight Reduction Temperature (° C.)

Using a thermogravimetry-differential thermal analyser (product name: "TG-DTA2000", manufactured by Mac Science Co. Ltd.), testing was conducted under the following conditions: Nitrogen flow rate: 100 ml/minute, heating rate: 10° C./minute, and weight of sample: 10 mg. The higher the 10% weight reduction temperature, the greater the thermal stability the sample has.

7) Alkali Resistance

Using a sample prepared by grinding and mixing 0.1 g of amide-based compound mixture or all-trans compound and 0.1 g of calcium hydroxide (powder) using an agate mortar, weight reduction of the sample was measured on a thremogravimetry-differential thermal analyzer (product name "TG-DTA 2000", manufactured by Mac Science Co. Ltd.) under the following conditions:

Nitrogen flow rate: 100 ml/minute,

Temperature: Elevated at 50° C./minute to 300° C., and held at 300° C. for 60 minutes Weight of sample: 10 mg.

The weight reduction at 5 minutes after reaching 300° C. was measured, and percent weight reduction (PWR) was calculated based on the weight of the sample. The smaller the percent weight reduction, the better the alkali resistance.

Example 1

(1) In a four-necked 500 ml flask equipped with a stirrer, a thermometer, a condenser and a gas inlet were placed 9.7 g of PTC (0.055 moles) and 100 g of N-methyl-2-pyrrolidone, and the PTC was completely dissolved with stirring under nitrogen atmosphere at room temperature. Subsequently, 20.5 g (0.1815 moles) of 2-methylcyclohexylamine (trans isomer: cis isomer=100.0:0.0, GLC composition %), 56.3 g (0.1815 moles) of triphenyl phosphite, 14.4 g (0.1815 moles) of pyridine and 50 g of N-methyl-2-pyrrolidone were added thereto, and the reaction was carried out with stirring under nitrogen atmosphere for 4 hours at 100° C. After cooling, the reaction solution was slowly pored into a mixture of 500 ml of isopropyl alcohol and 500 ml of water, and the resulting mixture was stirred at 40 to 50° C. for one hour, and white precipitate thus formed was then filtered off. The obtained white solid was washed twice with 500 ml of isopropyl alcohol at 40 to 50° C., and dried at 100° C. and 133 Pa for 6 hours.

The obtained dry product was pulverized in a mortar and passed through a standard sieve having openings of 106 μm (JIS Z-8801) to give 20.3 g (80% yield) of 1,2,3-propanetricarboxylic acid tris(2-methylcyclohexylamide) (hereinafter referred to as "PTC-2MeCHA").

The melting point of the thus obtained white powder and the trans-2-methylcyclohexylamine residue absorbance proportion (Ctrans) were measured. Table 1 shows the evaluation results. Table 1 also shows the characteristic infrared absorptions of the obtained white solid (C=O stretching vibration (amide I absorption band) and N—H deformation vibration (amide II absorption band)), 10% weight reduction temperature and alkali resistance (PWR).

(2) The unreacted 2-methylcyclohexylamine recovered after the above amidation reaction was subjected to GLC analysis to measure the trans:cis ratio thereof. It was found that the trans:cis ratio of the unreacted amine was 100:0, which was in agreement with the trans:cis ratio (100:0, GLC composition %) of the 2-methylcyclohexylamine used as the starting material.

The product amide obtained above, when treated at a temperature condition similar to that used in the amidation reaction (room temperature to 280° C.), had a FT-IR spectrum and a melting point that are in full agreement with those measured before the treatment, verifying that the stereo configuration was not altered by the amidation reaction.

In view of the above results, it was confirmed that the trans-configured moiety:cis-configured moiety ratio of the amide structure of the product amide-based compound of this Example 1 is identical to the trans:cis ratio (GLC %, i.e., mole %) of the amine starting material.

In each of Examples 2-16 and Comparative Examples 1-16, it was confirmed in the same manner as above that the ratio of the trans-configured moiety:cis-configured moiety of the amide structure of the product amide-based compound mixture or all-trans amide-based compound was identical to the trans:cis ratio (GLC %, i.e., mole %) of the amine starting material.

(3) Subsequently, to 100 parts by weight of isotactic homopolypropylene resin (MFR=30 g/10 minutes, hereinafter referred to as "h-PP") was added 0.2 part by weight of PTC-2MeCHA prepared by the above-described method. Further added thereto were 0.05 part by weight of tetrakis[methylene-3-(3,5-di-t-butyl-4-hydroxyphenyl)propionate]methane (manufactured by Ciba Specialty Chemicals Inc., product name: "IRGANOX 1010"), 0.05 part by weight of tris(2,4-di-t-butylphenyl)phosphite (manufactured by Ciba Specialty Chemicals Inc., product name: "IRGAFOS 168") and 0.05 part by weight of calcium stearate, and the mixture was then dry blended using a Henschel mixer for 5 minutes at 1000 rpm.

The obtained mixture was subjected to melt-kneading at a resin temperature of 240° C. using a single screw extruder having a diameter of 25 mm. The extruded strand was cooled with water, and the thus obtained strand was then cut, giving a polyolefin resin composition in the form of pellets.

The obtained pellets were injection molded at a resin temperature of 240° C. and a mold temperature of 40° C. to produce polyolefin resin molded articles (test pieces) with different sizes. One of them was a test piece for measuring haze and the size thereof was 70 mm×40 mm×1 mm, and the other was a test piece for measuring flexural modulus and the size thereof was 90 mm×10 mm×4 mm. The haze value, crystallization temperature and flexural modulus of the obtained test piece were measured. Table 1 shows the results.

Example 2

The procedure of Example 1 was repeated except that 2-methylcyclohexylamine (trans isomer:cis isomer=90.3:9.7, GLC composition %) was used in place of the 2-methylcyclohexylamine with trans isomer content of 100%. Table 1 shows the evaluation results. PTC-2MeCHA obtained by the reaction was 20.3 g (80% yield).

Example 3

The procedure of Example 1 was repeated except that 2-methylcyclohexylamine (trans isomer:cis isomer=77.2:22.8, GLC composition %) was used in place of the 2-methylcyclohexylamine with trans isomer content of 100%. Table 1 shows the evaluation results. PTC-2MeCHA obtained by the reaction was 20.0 g (79% yield).

Example 4

The procedure of Example 1 was repeated except that 2-methylcyclohexylamine (trans isomer:cis isomer=71.9:28.1, GLC composition %) was used in place of the 2-methylcyclohexylamine with trans isomer content of 100%. Table 1 shows the evaluation results. PTC-2MeCHA obtained by the reaction was 19.9 g (78% yield).

Comparative Example 1

The procedure of Example 1 was repeated except that 2-methylcyclohexylamine (trans isomer:cis isomer=68.2:31.8, GLC composition %) was used in place of the 2-methylcyclohexylamine with trans isomer content of 100%. Table 1 shows the evaluation results. PTC-2MeCHA obtained by the reaction was 19.3 g (76% yield).

Comparative Example 2

The procedure of Example 1 was repeated except that 2-methylcyclohexylamine (trans isomer:cis isomer=58.9:41.1, GLC composition %) was used in place of the 2-methylcyclohexylamine with trans isomer content of 100%. Table 1 shows the evaluation results. PTC-2MeCHA obtained by the reaction was 19.3 g (76% yield).

Comparative Example 3

The procedure of Example 1 was repeated except that 2-methylcyclohexylamine (trans isomer:cis isomer=50.4:49.6, GLC composition %) was used in place of the 2-methylcyclohexylamine with trans isomer content of 100%. Table 1 shows the evaluation results. PTC-2MeCHA obtained by the reaction was 18.0 g (71% yield).

Comparative Example 4

The procedure of Example 1 was repeated except that 2-methylcyclohexylamine (trans isomer:cis isomer=26.4:73.6, GLC composition %) was used in place of the 2-methylcyclohexylamine with trans isomer content of 100%. Table 1 shows the evaluation results. PTC-2MeCHA obtained by the reaction was 15.5 g (61% yield).

Comparative Example 5

The procedure of Example 1 was repeated except that 2-methylcyclohexylamine (trans isomer:cis isomer=1.0:99.0, GLC composition %) was used in place of the 2-methylcyclohexylamine with trans isomer content of 100%. Table 1 shows the evaluation results. PTC-2MeCHA obtained by the reaction was 11.7 g (46% yield).

Example 5

The procedure of Example 1 was repeated except that 9.4 g (0.04 mole) of 1,2,3,4-butanetetracarboxylic acid was used in place of PTC, and that the amounts of other materials were changed to 19.9 g (0.176 mole) of 2-methylcyclohexylamine (trans isomer:cis isomer=100.0:0.0, GLC composition %), 54.6 g (0.176 mole) of triphenyl phosphite, and 13.9 g (0.176 mole) of pyridine (but the amount of N-methyl-2-pyrrolidone was not changed). Table 1 shows the evaluation results. The reaction gave 16.0 g (yield 65%) of 1,2,3,4-butanetetracarboxylic acid tetrakis(2-methylcyclohexylamide)(hereunder referred to as "BTC-2MeCHA").

Example 6

The procedure of Example 5 was repeated except that 2-methylcyclohexylamine (trans isomer:cis isomer=90.3:9.7, GLC composition %) was used in place of the 2-methylcyclohexylamine with trans isomer content of 100%. Table 1 shows the evaluation results. BTC-2MeCHA obtained by the reaction was 18.7 g (76% yield).

Example 7

The procedure of Example 5 was repeated except that 2-methylcyclohexylamine (trans isomer:cis isomer=77.2:22.8, GLC composition %) was used in place of the 2-methylcyclohexylamine with trans isomer content of 100%. Table 1 shows the evaluation results. BTC-2MeCHA obtained by the reaction was 18.7 g (yield 76%).

Example 8

The procedure of Example 5 was repeated except that 2-methylcyclohexylamine (trans isomer:cis isomer=71.9:28.1, GLC composition %) was used in place of the 2-methylcyclohexylamine with trans isomer content of 100%. Table 1 shows the evaluation results. BTC-2MeCHA obtained by the reaction was 18.7 g (76% yield).

Comparative Example 6

The procedure of Example 5 was repeated except that 2-methylcyclohexylamine (trans isomer:cis isomer=69.0:31.0, GLC composition %) was used in place of the 2-methylcyclohexylamine with trans isomer content of 100%. Table 1 shows the evaluation results. BTC-2MeCHA obtained by the reaction was 18.7 g (76% yield).

Comparative Example 7

The procedure of Example 5 was repeated except that 2-methylcyclohexylamine (trans isomer:cis isomer=54.1:45.9, GLC composition %) was used in place of the 2-methylcyclohexylamine with trans isomer content of 100%. Table 1 shows the evaluation results. BTC-2MeCHA obtained by the reaction was 18.7 g (76% yield).

Comparative Example 8

The procedure of Example 5 was repeated except that 2-methylcyclohexylamine (trans isomer:cis isomer=2.8:97.2, GLC composition %) was used in place of the 2-methylcyclohexylamine with trans isomer content of 100%. Table 1 shows the evaluation results. BTC-2MeCHA obtained by the reaction was 19.4 g (79% yield).

TABLE 1

| | Content of amine trans isomer (%) | Resin | Amide compound | C trans (%) | Amide I absorption band (cm$^{-1}$) | Amide II absorption band (cm$^{-1}$) | m.p (°C.) | 10% weight reduction temperature (°C.) | Alkali resistance PWR (%) | Haze (%) | Tc (C°) | Flexural modulus (kg/mm$^2$) |
|---|---|---|---|---|---|---|---|---|---|---|---|---|
| Ex. 1 | 100.0 | h-PP | PTC-2MeCHA | 72.0 | 1643 | 1544 | 342.9 | 352 | 3.6 | 20 | 125 | 206 |
| Ex. 2 | 90.3 | h-PP | PTC-2MeCHA | 67.0 | 1643 | 1543 | 332.6 | 348 | — | 19 | 121 | 203 |
| Ex. 3 | 77.2 | h-PP | PTC-2MeCHA | 60.1 | 1643 | 1542 | 321.0 | 342 | — | 19 | 120 | 200 |
| Ex. 4 | 71.9 | h-PP | PTC-2MeCHA | 57.3 | 1643 | 1542 | 316.9 | 339 | 7.0 | 19 | 120 | 200 |
| Comp. Ex. 1 | 68.2 | h-PP | PTC-2MeCHA | 55.4 | 1643 | 1542 | 314.8 | 337 | 11.8 | 19 | 120 | 200 |
| Comp. Ex. 2 | 58.9 | h-PP | PTC-2MeCHA | 50.5 | 1643 | 1542 | 302.4 | — | — | 21 | 120 | 199 |
| Comp. Ex. 3 | 50.4 | h-PP | PTC-2MeCHA | 46.1 | 1643 | 1542 | 296.4 | — | — | 25 | 120 | 196 |
| Comp. Ex. 4 | 26.4 | h-PP | PTC-2MeCHA | 33.5 | 1643 | 1542 | 270.5 | — | — | 52 | 120 | 169 |
| Comp. Ex. 5 | 1.0 | h-PP | PTC-2MeCHA | 19.7 | 1643 | 1542 | 226.0 | — | — | 65 | 110 | 146 |
| Ex. 5 | 100.0 | h-PP | BTC-2MeCHA | 71.5 | 1639 | 1542 | 378.8 | 337 | 4.8 | 38 | 126 | 217 |
| Ex. 6 | 90.3 | h-PP | BTC-2MeCHA | 67.4 | 1639 | 1542 | 373.8 | 331 | — | 41 | 125 | 214 |
| Ex. 7 | 77.2 | h-PP | BTC-2MeCHA | 61.9 | 1639 | 1540 | 363.9 | 330 | — | 39 | 125 | 213 |
| Ex. 8 | 71.9 | h-PP | BTC-2MeCHA | 59.6 | 1639 | 1540 | 360.0 | 327 | 21.4 | 39 | 125 | 211 |
| Comp. Ex. 6 | 69.0 | h-PP | BTC-2MeCHA | 58.4 | 1639 | 1540 | 357.9 | 326 | 27.5 | 39 | 125 | 210 |
| Comp. Ex. 7 | 54.1 | h-PP | BTC-2MeCHA | 52.1 | 1639 | 1540 | 347.5 | — | — | 34 | 125 | 200 |
| Comp. Ex. 8 | 2.8 | h-PP | BTC-2MeCHA | 30.4 | 1640 | 1536 | 310.2 | — | — | 53 | 123 | 178 |

Example 9

The procedure of Example 1 was repeated except that an isotactic random polypropylene resin (MFR=20 g/10 minutes, hereinafter referred to as "r-PP") having an ethylene content of 3.0 wt. % was used in place of h-PP, and the evaluation results thereof are shown in Table 2.

Example 10

The procedure of Example 2 was repeated except that r-PP was used in place of h-PP, and the evaluation results thereof are shown in Table 2.

Example 11

The procedure of Example 3 was repeated except that r-PP was used in place of h-PP, and the evaluation results thereof are shown in Table 2.

Example 12

The procedure of Example 4 was repeated except that r-PP was used in place of h-PP, and the evaluation results thereof are shown in Table 2.

Comparative Example 9

The procedure of Comparative Example 1 was repeated except that r-PP was used in place of h-PP, and the evaluation results thereof are shown in Table 2.

Comparative Example 10

The procedure of Comparative Example 2 was repeated except that r-PP was used in place of h-PP, and the evaluation results thereof are shown in Table 2.

Comparative Example 11

The procedure of Comparative Example 3 was repeated except that r-PP was used in place of h-PP, and the evaluation results thereof are shown in Table 2.

Comparative Example 12

The procedure of Comparative Example 4 was repeated except that r-PP was used in place of h-PP, and the evaluation results thereof are shown in Table 2.

Comparative Example 13

The procedure of Comparative Example 5 was repeated except that r-PP was used in place of h-PP, and the evaluation results thereof are shown in Table 2.

Example 13

The procedure of Example 5 was repeated except that r-PP was used in place of h-PP, and the evaluation results thereof are shown in Table 2.

Example 14

The procedure of Example 6 was repeated except that r-PP was used in place of h-PP, and the evaluation results thereof are shown in Table 2.

Example 15

The procedure of Example 7 was repeated except that r-PP was used in place of h-PP, and the evaluation results thereof are shown in Table 2.

Example 16

The procedure of Example 8 was repeated except that r-PP was used in place of h-PP, and the evaluation results thereof are shown in Table 2.

Comparative Example 14

The procedure of Comparative Example 6 was repeated except that r-PP was used in place of h-PP, and the evaluation results thereof are shown in Table 2.

Comparative Example 15

The procedure of Comparative Example 7 was repeated except that r-PP was used in place of h-PP, and the evaluation results thereof are shown in Table 2.

Comparative Example 16

The procedure of Comparative Example 8 was repeated except that r-PP was used in place of h-PP, and the evaluation results thereof are shown in Table 2.

TABLE 2

| | Content of amine trans isomer (%) | Resin | Amide compound | Ctrans (%) | Melting point (°C.) | 10% weight reduction temperature (°C.) | Haze value (%) | Tc (°C.) | Flexural modulus (kg/mm$^2$) |
|---|---|---|---|---|---|---|---|---|---|
| Ex. 9 | 100.0 | r-PP | PTC-2MeCHA | 72.0 | 342.9 | 352 | 12 | 115 | 132 |
| Ex. 10 | 90.3 | r-PP | PTC-2MeCHA | 67.0 | 332.6 | 348 | 11 | 106 | 127 |
| Ex. 11 | 77.2 | r-PP | PTC-2MeCHA | 60.1 | 321.0 | 342 | 10 | 106 | 127 |
| Ex. 12 | 71.9 | r-PP | PTC-2MeCHA | 57.3 | 316.9 | 339 | 10 | 106 | 127 |
| Comp. Ex. 9 | 68.2 | r-PP | PTC-2MeCHA | 55.4 | 314.8 | 337 | 10 | 106 | 127 |
| Comp. Ex. 10 | 58.9 | r-PP | PTC-2MeCHA | 50.5 | 302.4 | — | 11 | 106 | 127 |
| Comp. Ex. 11 | 50.4 | r-PP | PTC-2MeCHA | 46.1 | 296.4 | — | 11 | 106 | 127 |
| Comp. Ex. 12 | 26.4 | r-PP | PTC-2MeCHA | 33.5 | 270.5 | — | 23 | 106 | 118 |
| Comp. Ex. 13 | 1.0 | r-PP | PTC-2MeCHA | 19.7 | 226.0 | — | 72 | 99 | 91 |
| Ex. 13 | 100.0 | r-PP | BTC-2MeCHA | 71.5 | 378.8 | 337 | 28 | 117 | 133 |
| Ex. 14 | 90.3 | r-PP | BTC-2MeCHA | 67.4 | 373.8 | 331 | 30 | 116 | 130 |
| Ex. 15 | 77.2 | r-PP | BTC-2MeCHA | 61.9 | 363.9 | 330 | 27 | 116 | 130 |
| Ex. 16 | 71.9 | r-PP | BTC-2MeCHA | 59.6 | 360.0 | 327 | 26 | 116 | 129 |

TABLE 2-continued

| | Content of amine trans isomer (%) | Resin | Amide compound | Ctrans (%) | Melting point (°C.) | 10% weight reduction temperature (°C.) | Haze value (%) | Tc (°C.) | Flexural modulus (kg/mm²) |
|---|---|---|---|---|---|---|---|---|---|
| Comp. Ex. 14 | 69.0 | r-PP | BTC-2MeCHA | 58.4 | 357.9 | 326 | 26 | 116 | 129 |
| Comp. Ex. 15 | 54.1 | r-PP | BTC-2MeCHA | 52.1 | 347.5 | — | 23 | 115 | 122 |
| Comp. Ex. 16 | 2.8 | r-PP | BTC-2MeCHA | 30.4 | 310.2 | — | 32 | 108 | 119 |

The following are clear from the results shown in Tables 1 and 2.

(1) With regard to the thermal stability of the all-trans amide-based compounds or amide-based compound mixtures of the invention, as the content of trans-2-alkylcyclohexylamine residue (or Ctrans value) increases, the melting point and the 10% weight reduction temperature increase. When the content is at least 70 mole % (Examples 1 to 16), the melting point and 10% weight reduction temperature are higher than those of the amide-based compound mixtures wherein the contents are less than 70 mole % (Comparative Examples 1 to 16), exhibiting significant improvement in thermal stability of the nucleating agents themselves.

Furthermore, the nucleating agents of the invention having a trans-2-alkylcyclohexylamine residue of at least 70 mole % have improved alkali resistance, compared with the amide-based nucleating agents wherein the contents are less than 70 mole %.

Polyolefin resins contain an alkaline substance (such as calcium stearate, calcium hydroxide, etc.) as an agent for neutralizing a polymerization catalyst. Therefore, nucleating agents are required to have alkali resistance. The excellent alkali resistance of the amide-based nucleating agent of the invention is industrially advantageous.

(2) The physical properties of the molded articles are also improved with the increase in trans-2-alkylcyclohexylamine residue content. Specifically, as the trans-2-alkylcyclohexylamine residue content increases, the physical properties of each molded article are improved, and even with a trans-2-alkylcyclohexylamine residue content of 68.2 mole % or 69 mole % (Comparative Examples 1, 6, 9 and 14), excellent transparency (haze value), crystallization temperature (Tc) and flexural modulus are exhibited; however, when the trans-2-alkylcyclohexylamine residue content is 70 to 100 mole % (Examples 1 to 16), excellent transparency, crystallization temperature and flexural modulus are substantially maintained or further improved.

(3) Therefore, when the thermal stability and other properties of the amide-based nucleating agent and various properties of the molded articles are totally taken into consideration, the trans-2-alkylcyclohexylamine residue content is preferably at least 70 mole %, particularly 70 to 90 mole %, and more preferably 70 to 80 mole %.

INDUSTRIAL APPLICABILITY

According to the present invention, when the trans structure content of a stereoisomeric 2-alkylcyclohexylamine residue constituting the all-trans amide-based compound or the mixture of the amide-based compounds represented by General Formula (1) is within the range of 70 to 100 mole %, the all-trans amide-based compound or the amide-based compound mixture exhibits excellent thermal stability and, by incorporating such an amide-based compound or mixture, or a nucleating agent comprising such an amide-based compound or mixture, into a polyolefin resin, it is possible to obtain polyolefin resin compositions and molded articles having excellent transparency, crystallizability and rigidity.

The invention claimed is:

1. A mixture of at least two amide-based compounds represented by General Formula (1):

$$R^1\text{---}(CONHR^2)_a \quad (1)$$

wherein a represents an integer of 2 to 6, $R^1$ represents a $C_{2-30}$ saturated or unsaturated aliphatic polycarboxylic acid residue, and said aliphatic polycarboxylic acid residue has a valency of 2 to 6, and the two to six $R^2$ groups are the same or different, and each represent a trans-2-alkylcyclohexylamine residue represented by General Formula (a):

(a)

wherein $R^3$ represents a $C_{1-10}$ linear or branched alkyl group, or a cis-2-alkylcyclohexylamine residue represented by General Formula (b):

(b)

wherein $R^3$ represents a $C_{1-10}$ linear or branched alkyl group, the trans-2-alkylcyclohexylamine residue represented by General Formula (a) being present in a proportion of at least 70 mole % but less than 100 mole % of the total 2-alkylcyclohexylamine residues in the mixture.

2. A mixture according to claim 1, wherein the trans-2-alkylcyclohexylamine residue represented by General Formula (a) is present in a proportion of at least 71.9 mole % but less than 100 mole % of the total 2-alkylcyclohexylamine residues in the mixture.

3. A mixture according to claim 1, wherein $R^3$ is a $C_{1-6}$ linear or branched alkyl group.

4. A mixture according to claim 1, wherein $R^3$ is methyl.

5. A mixture according to claim 1, wherein R¹ is a 1,2,3-propanetricarboxylic acid residue or a 1,2,3,4-butanetetracarboxylic acid residue.

6. A mixture according to claim 1, wherein R¹ is a 1,2,3-propanetricarboxylic acid residue, and the mixture has a trans 2-alkylcyclohexylamine residue absorbance proportion (Ctrans) of at least 56.3% but less than 72.0% as defined by equation (E):

$$Ctrans(\%) = [Atrans/(Atrans + Acis)] \cdot 100 \qquad (E)$$

wherein
- Atrans represents the absorbance, as measured by FT-IR spectroscopy (Fourier Transform Infrared Spectroscopy), at a wavenumber at which the N—H stretching vibration absorption signal of the trans-2-alkylcyclohexylamine residue represented by General Formula (a) of the corresponding all-trans amide-based compound appears, and
- Acis represents the absorbance, as measured by FT-IR spectroscopy (Fourier Transform Infrared Spectroscopy), at a wavenumber at which the N—H stretching vibration absorption signal of the cis-2-alkylcyclohexylamine residue represented by General Formula (b) of the corresponding all-cis amide-based compound appears.

7. A mixture according to claim 1, wherein R¹ is a 1,2,3,4-butanetetracarboxylic acid residue, and the mixture has a trans 2-alkylcyclohexylamine residue absorbance proportion (Ctrans) of at least 58.8% but less than 71.5% as defined by equation (E):

$$Ctrans(\%) = [Atrans/(Atrans + Acis)] \cdot 100 \qquad (E)$$

wherein
- Atrans represents the absorbance, as measured by FT-IR spectroscopy (Fourier Transform Infrared Spectroscopy), at a wavenumber at which the N—H stretching vibration absorption signal of the trans-2-alkylcyclohexylamine residue represented by General Formula (a) of the corresponding all-trans amide-based compound appears, and
- Acis represents the absorbance, as measured by FT-IR spectroscopy (Fourier Transform Infrared Spectroscopy), at a wavenumber at which the N—H stretching vibration absorption signal of the cis-2-alkylcyclohexylamine residue represented by General Formula (b) of the corresponding all-cis amide-based compound appears.

8. A process for producing a mixture of amide-based compounds represented by General Formula (1):

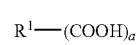

$$R^1—(CONHR^2)_a \qquad (1)$$

wherein
- a represents an integer of 2 to 6,
- R¹ represents a $C_{2-30}$ saturated or unsaturated aliphatic polycarboxylic acid residue, and said aliphatic polycarboxylic acid residue has a valency of 2 to 6, and
- the two to six R² groups are the same or different, and each represent a trans-2-alkylcyclohexylamine residue represented by General Formula (a):

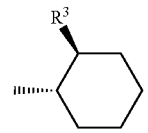
(a)

wherein R₃ represents a $C_{1-10}$ linear or branched alkyl group, or a cis-2-alkylcyclohexylamine residue represented by General Formula (b):

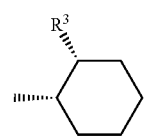
(b)

wherein R³ represents a $C_{1-10}$ linear or branched alkyl group, the trans-2-alkylcyclohexylamine residue represented by General Formula (a) being present in a proportion of at least 70 mole % but less than 100 mole % of the total 2-alkylcyclohexylamine residues in the mixture, the process comprising subjecting, to amidation reaction, a polycarboxylic acid represented by General Formula (2):

$$R^1—(COOH)_a \qquad (2)$$

wherein R¹ represents a $C_{2-30}$ saturated or unsaturated aliphatic polycarboxylic acid residue, and a represents an integer of 2 to 6 or a reactive derivative thereof, and an amine mixture of (i) a trans-2-alkylcyclohexylamine represented by General Formula (3a):

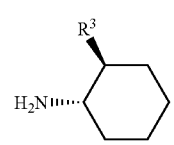
(3a)

wherein R³ represents a $C_{1-10}$ linear or branched alkyl group, and (ii) a cis-2-alkylcyclohexylamine represented by General Formula (3b)

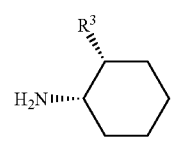
(3b)

wherein R³ represents a $C_{1-10}$ linear or branched alkyl group, the content of the trans-2-alkylcyclohexylamine in the amine mixture being at least 70% but less than 100% as determined by gas chromatography (GLC).

9. A method of using a mixture comprising at least two amide-based compounds, the method comprising incorporating a mixture according to claim 1 into a polyolefin resin to improve rigidity of a polyolefin resin molded product.

* * * * *